United States Patent
Giraldo Gomez et al.

(10) Patent No.: US 11,002,741 B2
(45) Date of Patent: May 11, 2021

(54) RATIOMETRIC AND MULTIPLEXED SENSORS FROM SINGLE CHIRALITY CARBON NANOTUBES

(71) Applicant: MASSACHUSETTS INSTITUTE OF TECHNOLOGY, Cambridge, MA (US)

(72) Inventors: Juan Pablo Giraldo Gomez, Claremont, CA (US); Markita Patricia Landry, Cambridge, MA (US); Michael S. Strano, Lexington, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 218 days.

(21) Appl. No.: 15/511,630

(22) PCT Filed: Sep. 18, 2015

(86) PCT No.: PCT/US2015/050885
§ 371 (c)(1),
(2) Date: Mar. 15, 2017

(87) PCT Pub. No.: WO2016/044698
PCT Pub. Date: Mar. 24, 2016

(65) Prior Publication Data
US 2017/0299601 A1    Oct. 19, 2017

Related U.S. Application Data
(60) Provisional application No. 62/052,767, filed on Sep. 19, 2014.

(51) Int. Cl.
| | | |
|---|---|---|
| *G01N 33/58* | (2006.01) | |
| *G01N 21/64* | (2006.01) | |
| *G01N 33/483* | (2006.01) | |
| *G01N 33/50* | (2006.01) | |
| *B82Y 15/00* | (2011.01) | |
| *C09K 11/02* | (2006.01) | |
| *C09K 11/65* | (2006.01) | |
| *B82Y 20/00* | (2011.01) | |
| *B82Y 40/00* | (2011.01) | |

(52) U.S. Cl.
CPC ............ *G01N 33/582* (2013.01); *B82Y 15/00* (2013.01); *C09K 11/025* (2013.01); *C09K 11/65* (2013.01); *G01N 21/6408* (2013.01); *G01N 21/6428* (2013.01); *G01N 21/6489* (2013.01); *G01N 33/4833* (2013.01); *G01N 33/5097* (2013.01); *B82Y 20/00* (2013.01); *B82Y 40/00* (2013.01); *G01N 2021/6415* (2013.01); *G01N 2021/6441* (2013.01); *Y10S 977/746* (2013.01); *Y10S 977/751* (2013.01); *Y10S 977/845* (2013.01); *Y10S 977/847* (2013.01); *Y10S 977/92* (2013.01)

(58) Field of Classification Search
CPC ......... B82Y 15/00; B82Y 20/00; B82Y 40/00; C09K 11/025; C09K 11/65; G01N 2021/6415; G01N 2021/6441; G01N 21/64; G01N 21/6408; G01N 21/6428; G01N 21/6489; G01N 33/4833; G01N 33/5097; G01N 33/582; Y10S 977/746; Y10S 977/751; Y10S 977/845; Y10S 977/847; Y10S 977/92; Y10T 436/177692; Y10T 436/20; Y10T 436/204998; Y10T 436/207497; Y10T 436/21; Y10T 436/212; Y10T 436/23
USPC ....... 436/116, 127, 133, 136, 139, 140, 145, 436/164, 172; 422/82.08
See application file for complete search history.

(56) References Cited

U.S. PATENT DOCUMENTS

| | | | |
|---|---|---|---|
| 8,460,608 B2 | 6/2013 | Strano et al. | |
| 8,486,709 B2 * | 7/2013 | Strano | ................ G01N 21/6428 436/116 |
| 8,765,488 B2 * | 7/2014 | Strano | .................... B82Y 15/00 435/14 |
| 2005/0129573 A1 | 6/2005 | Gabriel et al. | |
| 2011/0257033 A1* | 10/2011 | Strano | .................. G01N 33/542 506/9 |
| 2013/0035567 A1 | 2/2013 | Strano et al. | |
| 2014/0234856 A1 | 8/2014 | Reuel et al. | |
| 2015/0047074 A1* | 2/2015 | Strano | ..................... A01H 5/00 800/298 |
| 2015/0056142 A1* | 2/2015 | Tao | .................... A61K 49/0021 424/9.6 |

FOREIGN PATENT DOCUMENTS
WO    2004/043857 A2    5/2004

OTHER PUBLICATIONS

Giraldo et al. Small, vol. 11. No. 32, May 2015, pp. 3973-3984.*
Notification Concerning Transmittal of International Preliminary Report on Patentability (Chapter I of the Patent Cooperation Treaty) dated Mar. 30, 2017, issued in International Application No. PCT/US2015/050885.
International Search Report dated Jan. 29, 2016, issued in International Application No. PCT/US2015/050885.
Written Opinion of the International Searching Authority dated Jan. 29, 2016, issued in International Application No. PCT/US2015/050885.
Giraldo, JP et al. "Plant nanobionics approach to augment photosynthesis and biochemical sensing." Nature materials. Mar. 2014, vol. 13, No. 4, pp. 400-408; abstract; p. 402, paragraph 2.

(Continued)

*Primary Examiner* — Maureen Wallenhorst
(74) *Attorney, Agent, or Firm* — Honigman LLP

(57) ABSTRACT

A single chirality single walled carbon nanotubes (SWNT), and combinations thereof, can be used to detect trace levels of chemical compounds in vivo with high selectivity.

33 Claims, 13 Drawing Sheets

(56) References Cited

OTHER PUBLICATIONS

Zhang, L. et al. "A carbon nanotubes based ATP apta-sensing platform and its application in cellular assay." Biosensors and Bioelectronics. 2010, vol. 25, No. 8 pp. 1897-1901; abstract.

Ruhal, A. et al. "Immobilization of malate dehydrogenase on carbon nanotubes for development of malate biosensor." Cellular & Molecular Biology. 2012, vol. 58, No. 1, pp. 15-20; abstract; p. 16, paragraphs 2-3.

Liu, R. et al. "Detection of pH Change in Cytoplasm of Live Myocardial Ischemia Cells via the ssDNA-SWCNTs Nanoprobes." Analytical chemistry. Feb. 2014, vol. 86, No. 6, pp. 3048-3052; abstract.

Kruss, S. et al. "Neurotransmitter detection using corona phase molecular recognition on fluorescent single-walled carbon nanotube sensors." Journal of the American chemical Society. 2013, vol. 136, No. 2, pp. 713-724.

* cited by examiner

Hydrogen Peroxide

Nitric oxide

| Logistic fit for H2O2 (R1/2) | | |
|---|---|---|
| Model(R1/2) | Logistic | |
| Equation | y = A2 + (A1-A2)/(1 + (x/x0)^p) | |
| Reduced Chi-Sqr | 5.04E-05 | |
| Adj. R-Square | 0.99437 | |
| | Value | Standard Error |
| R1/2  A1 | 1.38062 | 0.00685 |
| A2 | 175.6199 | 15271.77 |
| x0 | 9.09E+06 | 1.24E+09 |
| p | 0.64776 | 0.08476 |
| EC20 | 1.07E+06 | |
| EC50 | 9.09E+06 | |
| EC80 | 7.73E+07 | |
| R2/1  A1 | 0.72766 | 0.00258 |
| A2 | -29.8872 | 964.8067 |
| x0 | 1.18E+07 | 7.06E+08 |
| p | 0.53931 | 0.06214 |
| EC20 | 902736.2 | |
| EC50 | 1.18E+07 | |
| EC80 | 1.54E+08 | |

FIG. 9A

| Model | Cubic | | |
|---|---|---|---|
| Equation | y = A + B*x + C*x^2 + D*x^3 | | |
| Reduced Chi-Sqr | 0.04004 | 0.00342 | |
| Adj. R-Square | 0.95849 | 0.90347 | |
| | | Value | Standard Error |
| R1/2 | A | 1.05216 | 0.12798 |
| | B | 0.01458 | 0.00188 |
| | C | -2.68E-05 | 7.34E-06 |
| | D | 2.01E-08 | 8.04E-09 |
| R2/1 | A | 0.9003 | 0.03743 |
| | B | -0.00542 | 5.49E-04 |
| | C | 1.47E-05 | 2.15E-06 |
| | D | -1.29E-08 | 2.35E-09 |

FIG. 9B

RATIOMETRIC AND MULTIPLEXED SENSORS FROM SINGLE CHIRALITY CARBON NANOTUBES

PRIORITY CLAIM

This application claims the benefit under 35 USC 371 to International Application No. PCT/US2015/050885, filed Sep. 18, 2015, which claims priority to U.S. Provisional Application No. 62/052,767, filed Sep. 19, 2014, each of which is incorporated by reference in its entirety.

STATEMENT REGARDING FEDERALLY SPONSORED RESEARCH OR DEVELOPMENT

This invention was made with government support under Grant Nos. CHE-1213622 and DBI-1103600 awarded by the National Science Foundation. The government has certain rights in the invention.

TECHNICAL FIELD

This invention relates to a ratiometric sensor from carbon nanotubes.

BACKGROUND

Single walled carbon nanotubes (SWNT) are promising platforms for sensing applications in photosynthetic organisms. They photoluminesce in the near infrared (NIR) in which plant tissues are relatively transparent, do not photobleach, and allow detection at the single particle level. See, Giraldo, J. et al. Plant nanobionics approach to augment photosynthesis and biochemical sensing. *Nat. Mater.* 13, 400-408 (2014), and Zhang, J. et al. Single molecule detection of nitric oxide enabled by d(AT)15 DNA adsorbed to near infrared fluorescent single-walled carbon nanotubes. *J. Am. Chem. Soc.* 133, 567-581 (2011), each of which is incorporated by reference in its entirety. SWNT are well suited for the detection of trace levels of chemical compounds with short lifetimes within plants and the environment such as hydrogen peroxide ($H_2O_2$) and nitric oxide (NO). Dyes with intrinsic fluorescence in visible wavelengths have been traditionally used for imaging $H_2O_2^3$ and $NO^4$. See, Rhee, S. G., Chang, T.-S., Jeong, W. & Kang, D. Methods for detection and measurement of hydrogen peroxide inside and outside of cells. *Mol. Cells* 29, 539-49 (2010), and Foissner, I., Wendehenne, D., Langebartels, C. & Durner, J. In vivo imaging of an elicitor-induced nitric oxide burst in tobacco. *The Plant journal* 23, 817-24 (2000), each of which is incorporated by reference in its entirety. Although these fluorophores enable imaging with cellular resolution, in real time, they present a set of complex problems for in vivo visualization in plant tissues. See, Swanson, S. J., Choi, W.-G., Chanoca, A. & Gilroy, S. In vivo imaging of Ca2+, pH, and reactive oxygen species using fluorescent probes in plants. *Annu. Rev. Plant Biol.* 62, 273-97 (2011), which is incorporated by reference in its entirety. Amplex red is widely used for imaging low concentrations of hydrogen peroxide but has been rarely used in plants due to its photodegradation. See, Driever, S. M., Fryer, M. J., Mullineaux, P. M. & Baker, N. R. in *Plant signal Transduct.* (Pfannschmidt, T.) 479, 109-116 (Humana Press, 2009), which is incorporated by reference in its entirety. The membrane permeable $H_2DCF$-DA dye has been commonly used in plants despite its relatively non-selectivity to reactive oxygen species (ROS) and susceptibility to photo-oxidation and photobleaching. Imaging of NO in living plant cells has been performed with diamionofluoresceins with the disadvantage that their fluorescein chromophore is responsive to changes in pH. See, Vitecek, J., Reinohl, V. & Jones, R. L. Measuring NO production in plant tissues and suspension cultured cells. *Mol. Plant* 1, 270-84 (2008), which is incorporated by reference in its entirety. In contrast, SWNT do not exhibit photodegradation and can be excited with light sources off-resonance of photosynthetic pigments. Furthermore, recent advances enable simple and fast delivery of SWNT to leaf living tissues, which has the potential to expand free radical imaging to any plant species. However, lack of specificity of SWNT NIR fluorescence response to biochemicals impairs their applications as highly selective photostable fluorescence sensors in vivo.

SUMMARY

A ratiometric SWNA sensor can be enabled by separation and functionalization of SWNT by their electronic type. A distinct SWNT chirality can be independently functionalized to recognize a specific biomolecule relative to another chirality that remains invariant to the analyte. In this way, an absolute measure of the analyte relative to an internal standard can be obtained. Independent functionalization of SWNT chiralities can be accomplished via rapid and efficient coating exchange of single chirality SDS-SWNT. The multiplexed NIR spectral signature can improve SWNT sensor quantification of biochemicals both in vitro and in vivo. This ratiometric optical sensing platform can enable the detection of trace biochemical compounds in complex environments such as strongly scattering media and biological tissues.

A composition can include a first plurality of nanoparticles having a first chirality and a second plurality of nanoparticles having a second chirality. A green plant can include such a composition. A composition can include a photocatalytic unit including an outer lipid membrane, and a plurality of nanoparticles having a single chirality contained within the outer lipid membrane of the photocatalytic unit. The photocatalytic unit can be a chloroplast, a cyanobacteria, or a bacterial species selected from the group consisting of *Chlorobiacea* spp., a *Chromaticacea* spp. and a *Rhodospirillacae* spp.

The plurality of nanoparticles can include a nanotube, a carbon nanotube, or a single-walled carbon nanotube. The plurality of nanoparticles can include a polymer, a polynucleotide, poly(AT), or a polysaccharide. The polysaccharide can be selected from the group consisting of dextran, pectin, hyaluronic acid, chitosan, and hydroxyethylcellulose. The polymer can include poly(vinyl acid). The plurality of nanoparticles can be carbon nanotubes or semiconductors.

The plurality of nanoparticles can be photoluminescent. The plurality of nanoparticles can emit near-infrared radiation. Each of the plurality of nanoparticles can be photoluminescent and the photoluminescence emission of the photoluminescent nanoparticle can be altered by a change in a stimulus. The stimulus can be the concentration of an analyte. The analyte can be a reactive oxygen species, nitric oxide, carbon dioxide, adenosine triphosphate, nicotinamide adenine dinucleotide phosphate, or oxygen. The stimulus can be the pH of the organelle.

A method for monitoring activity in a sample can include contacting a composition including a first plurality of nanoparticles having a first chirality and a second plurality of nanoparticles having a second chirality with the sample, measuring the photoluminescence emission of the composition at a first time point, measuring the photoluminescence emission of the composition at a second time point, and comparing the photoluminescence emission measured at the first time point to the photoluminescence emission measured at the second time point, wherein a change in the photoluminescence emission between the first time point and the second time point indicates a change in a stimulus within the sample.

The change in the photoluminescence emission can include a change in photoluminescence intensity, a change in peak wavelength, a Raman shift, or a combination thereof. The stimulus can be the concentration of an analyte. The analyte can be a reactive oxygen species, nitric oxide, carbon dioxide, adenosine triphosphate, nicotinamide adenine dinucleotide phosphate, oxygen, or nitroaromatic compounds. The stimulus can be pH of an organelle.

A method for monitoring a sample can include introducing a plurality of a first photoluminescent nanoparticle into the sample, wherein the first plurality of photoluminescent nanoparticle has a first chirality, introducing a plurality of a second photoluminescent nanoparticle into the sample, wherein the second plurality of photoluminescent nanoparticle has a second chirality, measuring the photoluminescence emission of the first plurality of photoluminescent nanoparticles and the second plurality of photoluminescent nanoparticles at a first time point, measuring the photoluminescence emission of the first plurality of photoluminescent nanoparticles and the second plurality of photoluminescent nanoparticles at a second time point, comparing the photoluminescence emission measured at the first time point to the photoluminescence emission measured at the second time point for the first plurality of photoluminescent nanoparticle, and comparing the photoluminescence emission measured at the first time point to the photoluminescence emission measured at the second time point for the second plurality of photoluminescent nanoparticle, wherein a change in the photoluminescence emission between the first time point and the second time point indicates a change in a stimulus within the sample.

A method of separating a plurality of nanoparticles can include suspending the plurality of nanoparticles in an aqueous medium with a surfactant, sonicating the medium of the plurality of nanoparticles, adding a polymer to the medium, and adding an alcohol dropwise while maintaining the mixing of alcohol and the medium. The surfactant can be sodium dodecyl sulfate. The alcohol can be methanol. The polymer is poly(vinyl) alcohol.

Other aspects, embodiments, and features will be apparent from the following description, the drawings, and the claims.

BRIEF DESCRIPTION OF THE DRAWINGS

FIG. 1A is a schematic showing the polymer in solution adsorbs to SWNT surface during bath sonication as MeOH is added dropwise. FIG. 1B is a graph depicting absorption spectra of single chirality 6,5 SWNT showing that coating exchange efficiency depends on the type of polymer. FIG. 1C is a graph depicting percent recovery of 6,5 SWNT after exchange of SDS with other coatings.

FIGS. 4A-4B are graphs showing 6,5 $ss(AT)_{15}$ and 6,5 PVA SWNT NIR fluorescence remained relatively constant after addition of hydrogen peroxide and nitric oxide, respectively. FIGS. 4C-4D are graphs showing 7,6 $ss(GT)_{15}$ SWNT quench in the presence of $H_2O_2$ and NO, respectively.

FIG. 5A shows leaf sections infiltrated with a 6,5 $ss(AT)_{15}$ and 7,6 $ss(GT)_{15}$ ratio sensor imaged in bright-field, in the NIR prior to addition of hydrogen peroxide, in the NIR microscope upon addition of hydrogen peroxide, a map of the hydrogen peroxide detection determined by the NIR intensity change in the leaf section that is the difference in intensity pre- and post-hydrogen peroxide addition, and traces of the ratiometric response (R) as a function of time. FIG. 5B is a graph showing hydrogen peroxide quenches 7,6 $ss(GT)_{15}$ by ~20%, whereas the intensity of 6,5 $ss(AT)_{15}$ remains constant.

FIG. 6A shows leaf sections infiltrated with a 6,5 PVA and 7,6 $ss(GT)_{15}$ ratio sensor were imaged in bright-field, in the NIR prior to addition of nitric peroxide, in the NIR upon addition of nitric oxide, a map of the nitric peroxide detection determined by the NIR intensity change in the leaf section that is the difference in intensity pre- and post-nitric peroxide addition, and traces of the ratiometric response (R) as a function of time. FIG. 6B is a graph showing intensity-time trace analysis of 6,5 PVA and 7,6 $ss(GT)_{15}$ peak intensity changes over time after NO addition.

FIGS. 9A-9B shows tables of logistic fit for ratio of intensity (R) changes over time in response to hydrogen peroxide (FIG. 9A) and nitric oxide (FIG. 9B) in vitro.

DETAILED DESCRIPTION

Figure 1A:
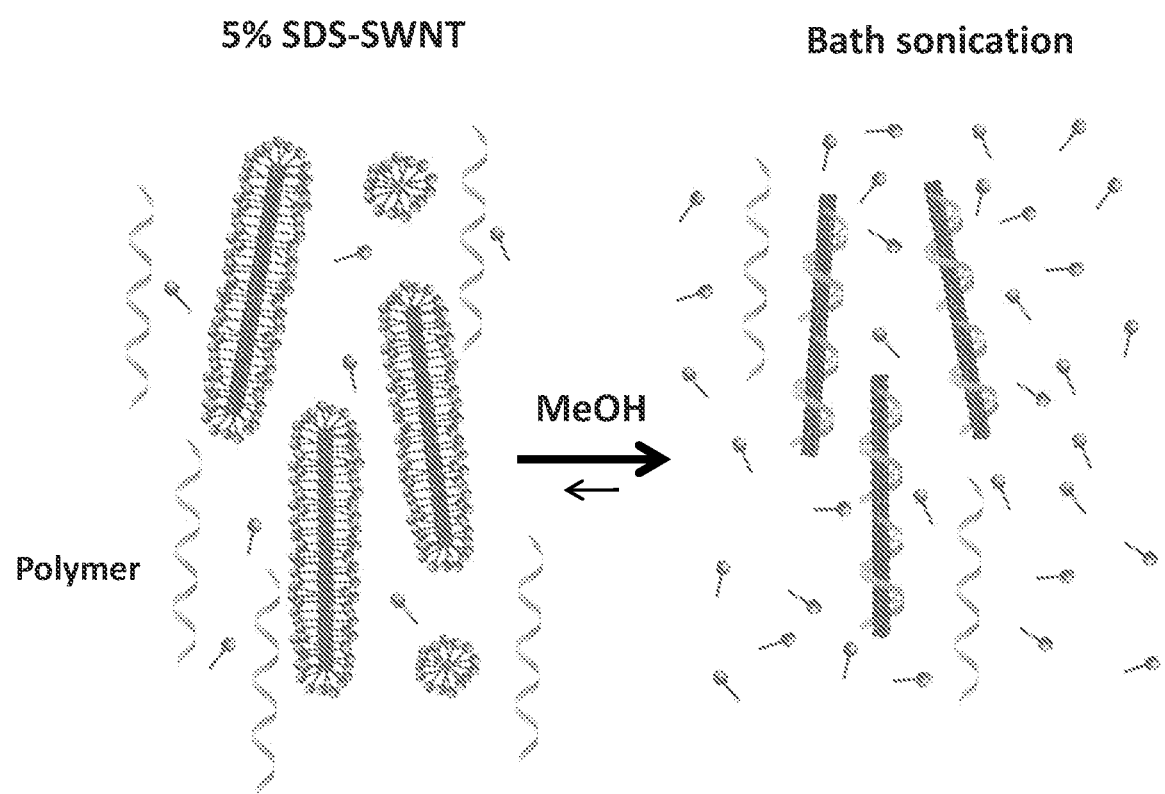
FIGS. 1A-1C show a method for rapid and efficient coating exchange of single chirality SWNT by sonication.

As used herein, the term "nanoparticle" refers to articles having at least one cross-sectional dimension of less than about 1 micron. A nanoparticle can also be referred to as a "nanostructure." A nanoparticle can have at least one cross-sectional dimension of less than about 500 nm, less than about 250 nm, less than about 100 nm, less than about 75 nm, less than about 50 nm, less than about 25 nm, less than about 10 nm, or, in some cases, less than about 1 nm. Examples of nanoparticle include nanotubes (e.g., carbon nanotubes), nanowires (e.g., carbon nanowires), graphene, and quantum dots, among others. In some embodiments, the nanoparticle can include a fused network of atomic rings, the atomic rings comprising a plurality of double bonds.

A nanoparticle can be a photoluminescent nanoparticle. A "photoluminescent nanoparticle," as used herein, refers to a class of nanoparticles that are capable of exhibiting photoluminescence. In some cases, photoluminescent nanoparticles can exhibit fluorescence. In some instances, photoluminescent nanoparticles exhibit phosphorescence. Examples of photoluminescent nanoparticles suitable for use include, but are not limited to, single-walled carbon nanotubes (SWCNTs), double-walled carbon nanotubes (DWCNTs), multi-walled carbon nanotubes (MWCNTs), semi-conductor quantum dots, semi-conductor nanowires, and graphene, among others.

A variety of nanoparticles can be used. Sometimes a nanoparticle can be a carbon-based nanoparticle. As used herein, a "carbon-based nanoparticle" can include a fused network of aromatic rings wherein the nanoparticle includes primarily carbon atoms. In some instances, a nanoparticle can have a cylindrical, pseudo-cylindrical, or horn shape. A carbon-based nanoparticle can include a fused network of at least about 10, at least about 50, at least about 100, at least about 1000, at least about 10,000, or, in some cases, at least about 100,000 aromatic rings. A carbon-based nanoparticle may be substantially planar or substantially non-planar, or may include a planar or non-planar portion. A carbon-based nanoparticle may optionally include a border at which the fused network terminates. For example, a sheet of graphene includes a planar carbon-containing molecule including a border at which the fused network terminates, while a carbon nanotube includes a non-planar carbon-based nanoparticle with borders at either end. In some cases, the border may be substituted with hydrogen atoms. In some cases, the border may be substituted with groups comprising oxygen atoms (e.g., hydroxyl).

In some embodiments, a nanoparticle can include or be a nanotube. The term "nanotube" is given its ordinary meaning in the art and can refer to a substantially cylindrical molecule or nanoparticle including a fused network of primarily six-membered rings (e.g., six-membered aromatic rings). In some cases, a nanotube can resemble a sheet of graphite formed into a seamless cylindrical structure. It should be understood that a nanotube may also include rings or lattice structures other than six-membered rings. Typically, at least one end of the nanotube may be capped, i.e., with a curved or non-planar aromatic group. A nanotube may have a diameter of the order of nanometers and a length on the order of microns, tens of microns, hundreds of microns, or millimeters, resulting in an aspect ratio greater than about 100, about 1000, about 10,000, or greater. In some embodiments, a nanotube can have a diameter of less than about 1 micron, less than about 500 nm, less than about 250 nm, less than about 100 nm, less than about 75 nm, less than about 50 nm, less than about 25 nm, less than about 10 nm, or, in some cases, less than about 1 nm.

In some embodiments, a nanotube may include a carbon nanotube. The term "carbon nanotube" can refer to a nanotube including primarily carbon atoms. Examples of carbon nanotubes can include single-walled carbon nanotubes (SWNTs), double-walled carbon nanotubes (DWNTs), multi-walled carbon nanotubes (MWNTs) (e.g., concentric carbon nanotubes), inorganic derivatives thereof, and the like. In some embodiments, a carbon nanotube can be a single-walled carbon nanotube. In some cases, a carbon nanotube can be a multi-walled carbon nanotube (e.g., a double-walled carbon nanotube).

In some embodiments, a nanoparticle can include non-carbon nanoparticles, specifically, non-carbon nanotubes. Non-carbon nanotubes may be of any of the shapes and dimensions outlined above with respect to carbon nanotubes. A non-carbon nanotube material may be selected from polymer, ceramic, metal and other suitable materials. For example, a non-carbon nanotube may include a metal such as Co, Fe, Ni, Mo, Cu, Au, Ag, Pt, Pd, Al, Zn, or alloys of these metals, among others. In some instances, a non-carbon nanotube may be formed of a semi-conductor such as, for example, Si. In some cases, a non-carbon nanotube may include a Group II-VI nanotube, wherein Group II includes Zn, Cd, and Hg, and Group VI includes O, S, Se, Te, and Po. In some embodiments, a non-carbon nanotube may include a Group III-V nanotube, wherein Group III includes B, Al, Ga, In, and Tl, and Group V includes N, P, As, Sb, and Bi. As a specific example, a non-carbon nanotube may include a boron-nitride nanotube. In other embodiments, the nanoparticle can be a ceramic, for example, a metal oxide, metal nitride, metal boride, metal phosphide, or metal carbide. In this example, the metal can be any metal, including Group I metal, Group II metal, Group III metal, Group IV metal, transition metal, lanthanide metal or actinide metal. For example, the ceramic can include one or more of metal, for example, Li, Na, K, Rb, Cs, Be, Mg, Ca, Sr, Ba, Sc, Y, La, Ce, Pr, Nd, Pm, Sm, Eu, Gd, Tb, Dy, Ho, Er, Tm, Yb, Lu, Ti, Zr, Hf, V, Nb, Ta, Cr, Mo, W, Mn, Tc, Re, Fe, Ru, Os, Co, Rh, Ir, Ni, Pd, Pt, Cu, Ag, Su, Zn, Cd, Hg, Al, Ga, In, Tl, Si, Ge, Sn, Pb or Bi.

In some embodiments, a nanotube may include both carbon and another material. For example, in some cases, a multi-walled nanotube may include at least one carbon-based wall (e.g., a conventional graphene sheet joined along a vector) and at least one non-carbon wall (e.g., a wall comprising a metal, silicon, boron nitride, etc.). In some embodiments, the carbon-based wall may surround at least one non-carbon wall. In some instances, a non-carbon wall may surround at least one carbon-based wall.

The term "quantum dot" is given its normal meaning in the art and can refer to semi-conducting nanoparticles that exhibit quantum confinement effects. Generally, energy (e.g., light) incident upon a quantum dot can excite the quantum dot to an excited state, after which, the quantum dot can emit energy corresponding to the energy band gap between its excited state and its ground state. Examples of materials from which quantum dots can be made include PbS, PbSe, CdS, CdSe, ZnS, and ZnSe, among others.

A photoluminescent nanoparticle can be, in some cases, substantially free of dopants, impurities, or other non-nanoparticle atoms. For example, in some embodiments, a nanoparticle can include a carbon nanoparticle that is substantially free of dopants. As a specific example, in some embodiments, a nanoparticle can include single-walled carbon nanotube that contains only aromatic rings (each of which contains only carbon atoms) within the shell portion of the nanotube. In other words, a nanoparticle can consist essentially of a single material, for example, carbon.

In some embodiments, a photoluminescent nanoparticle may emit radiation within a desired range of wavelengths. For example, in some cases, a photoluminescent nanoparticle may emit radiation with a wavelength between about 750 nm and about 1600 nm, or between about 900 nm and about 1400 nm (e.g., in the near-infrared range of wavelengths). In some embodiments, a photoluminescent nanoparticle may emit radiation with a wavelength within the visible range of the spectrum (e.g., between about 400 nm and about 700 nm).

In some embodiments, a photoluminescent nanoparticle may be substantially free of covalent bonds with other entities (e.g., other nanoparticles, a current collector, the surface of a container, a polymer, an analyte, etc.). The absence of covalent bonding between a photoluminescent nanoparticle and another entity may, for example, preserve the photoluminescent character of the nanoparticle. In some cases, single-walled carbon nanotubes or other photoluminescent nanoparticles may exhibit modified or substantially no fluorescence upon forming a covalent bond with another entity (e.g., another nanoparticle, a current collector, a surface of a container, and the like).

In some embodiments, a nanoparticle can include cerium oxide. A nanoparticle including cerium oxide can be referred to as nanoceria. A nanoparticle can be cerium oxide. A nanoparticle can also be conjugated to at least one cerium oxide nanoparticle. Conjugation can be direct or indirect. Conjugation can also be through a covalent bond, ionic bond or van der Waals interaction. A nanoparticle can be cross-linked with at least one cerium oxide nanoparticle, more specifically, cross-linked using via carbodiimide chemistry. In one example, a carbodiimide agent N-ethyl-N'-(3-dimethylaminopropyl) carbodiimide hydrochloride (EDAC) can be used.

A nanoparticle can be strongly cationic or anionic. Strongly cationic or anionic can mean that the nanoparticle (or other element) has a high magnitude of the zeta potential. For example, the nanoparticle can have a zeta potential of less than −10 mV or greater than 10 mV. In preferred embodiments, the nanoparticle can have a zeta potential of less than −20 mV or greater than 20 mV, a zeta potential of less than −30 mV or greater than 30 mV, or a zeta potential of less than −40 mV or greater than 40 mV.

A nanoparticle can include a coating or be suspended in a coating with a high magnitude of the zeta potential. A coating can be a polymer. A variety of polymers may be used in association with the embodiments described herein. In some cases, the polymer may be a polypeptide. In some embodiments, the length and/or weight of the polypeptide may fall within a specific range. For example, the polypeptide may include, in some embodiments, between about 5 and about 50, or between about 5 and about 30 amino acid residues. In some cases, the polypeptide may have a molecular weight of between about 400 g/mol and about 10,000 g/mol, or between about 400 g/mol and about 600 g/mol. Examples of protein polymers can include glucose oxidase, bovine serum albumin and alcohol dehydrogenase.

A polymer may include a synthetic polymer (e.g., polyvinyl alcohol, poly(acrylic acid), poly(ethylene oxide), poly(vinyl pyrrolidinone), poly(allyl amine), poly(2-vinylpyridine), poly(maleic acid), and the like), in some embodiments.

In some embodiments, the polymer may include an oligonucleotide. The oligonucleotide can be, in some cases, a single-stranded DNA oligonucleotide. The single-stranded DNA oligonucleotide can, in some cases, include a majority (>50%) A or T nucleobases. In some embodiments, single-stranded DNA oligonucleotide can include more than 75%, more than 80%, more than 90%, or more than 95% A or T nucleobases. In some embodiments, the single-stranded DNA oligonucleotide can include a repeat of A and T. For example, a oligonucleotide can be, in some cases, at least 5, at least 10, at least 15, between 5 and 25, between 5 and 15, or between 5 and 10 repeating units, in succession, of (GT) or (AT). Repeating units can include at least 2 nucleobases, at least 3 nucleobases, at least 4 nucleobases, at least 5 nucleotides long. The nucleobases described herein are given their standard one-letter abbreviations: cytosine (C), guanine (G), adenine (A), and thymine (T).

In some embodiments, the polymer can include a polysaccharide such as, for example, dextran, pectin, hyaluronic acid, hydroxyethylcellulose, amylose, chitin, or cellulose.

In preferred embodiments, the interaction between a polymer and a nanoparticle can be non-covalent (e.g., via van der Waals interactions); however, a polymer can covalently bond with a nanoparticle. In some embodiments, the polymer may be capable of participating in a pi-pi interaction with the nanostructure. A pi-pi interaction (a.k.a., "pi-pi stacking") is a phenomenon known to those of ordinary skill in the art, and generally refers to a stacked arrangement of molecules adopted due to interatomic interactions. Pi-pi interactions can occur, for example, between two aromatic molecules. If the polymer includes relatively large groups, pi-pi interaction can be reduced or eliminated due to steric hindrance. Hence, in certain embodiments, the polymer may be selected or altered such that steric hindrance does not inhibit or prevent pi-pi interactions. One of ordinary skill in the art can determine whether a polymer is capable or participating in pi-pi interactions with a nanostructure.

A nanoparticle can be contained within a chloroplast, as demonstrated more fully herein. A nanoparticle can traverse and/or localize within the outer membrane layer (i.e., lipid bilayer). The process can be complete and/or irreversible. Because other organelles include an outer membrane layer (i.e., lipid bilayer), a nanoparticle can be contained within other organelles. For example, other organelles that a nanoparticle can be introduced into can include a nucleus, endoplasmic reticulum, Golgi apparatus, chloroplast, chromoplast, gerontoplast, leucoplast, lysosome, peroxisome, glyoxysome, endosome, mitochondria or vacuole.

Thylakoids are a membrane-bound compartment inside a chloroplast. Cyanobacteria can also include thylakoids. In some embodiments, a nanoparticle can be associated with a thylakoid membrane within a chloroplast, cyanobacteria or other photocatalytic cell or organelle.

A nanoparticle can be contained within a photocatalytic unit, most preferably, including an outer lipid membrane (i.e., lipid bilayer). A photocatalytic unit can be a structure capable of performing photosynthesis or photocatalysis, preferably a cell or an organelle capable of performing photosynthesis or photocatalysis. For example, a photocatalytic unit can be a chloroplast, a cyanobacteria, or a bacterial species selected from the group consisting of *Chlorobiacea* spp., a *Chromaticacea* spp. and a *Rhodospirillacea* spp.

An organelle can be part of a cell, a cell can be part of a tissue, and a tissue can be part of an organism. A nanoparticle can be contained in a cell, in a tissue, or in an organelle. In one embodiment, a nanoparticle can be contained in a parenchyma cell, a collenchyma cell, or a sclerenchyma cell. In another embodiment, a nanoparticle can be contained in a xylem cell, a phloem cell, or an epidermal cell. In another embodiment, a nanoparticle can be contained in a cell membrane, a cell wall, a nuclear membrane, a plasmodesma, a cytoplasm, an endoplasmic reticulum, a mitochondrion, a vacuole, a platid, a leucoplast, a chromoplast, a golgi body, or a chloroplast. In another embodiment, a nanoparticle can be contained in a root, a stem, a leaf, a flower, or a reproductive structure. For example, a nanoparticle can be contained within a cell of a leaf of a plant. More to the point, a cell can be intact. In other words, the organelle may not be an isolated organelle, but rather, the organelle can be contained within the outer lipid membrane of a cell.

A nanoparticle that is independent of an organelle or cell can be free of lipids. An outer lipid membrane can enclose or encompass an organelle or cell. As the nanoparticle traverses the outer lipid membrane of an organelle or cell, lipids from the outer lipid membrane can associate or coat the nanoparticle. As a result, a nanoparticle inside the outer lipid membrane of an organelle or cell can be associated with or coated with lipids that originated in the organelle or cell.

Transport of a nanoparticle into an organelle or a cell can be a passive or active process. In some cases, transport across the outer lipid membrane can be independent of the temperature or light conditions.

Embedding a nanoparticle within an organelle or cell can be useful for monitoring the activity of the organelle or cell. For example, a nanoparticle, preferably a photoluminescent nanoparticle, can be introduced into the organelle or cell. Measurements of the photoluminescence of a photoluminescent nanoparticle can provide information regarding a stimulus within an organelle or cell. Measurements of the photoluminescence of a photoluminescent nanoparticle can be taken at a plurality of time points. A change in the photoluminescence emission between a first time point and a second time point can indicate a change in a stimulus within the organelle or cell.

In some embodiments, a change in the photoluminescence emission can include a change in the photoluminescence intensity, a change in an emission peak width, a change in an emission peak wavelength, a Raman shift, or combination thereof. One of ordinary skill in the art would be capable of calculating the overall intensity by, for example, taking the sum of the intensities of the emissions over a range of wavelengths emitted by a nanoparticle. In some cases, a nanoparticle may have a first overall intensity, and a second, lower overall intensity when a stimulus changes within the organelle or cell. In some cases, a nanoparticle may emit a first emission of a first overall intensity, and a second emission of a second overall intensity that is different from the first overall intensity (e.g., larger, smaller) when a stimulus changes within the organelle or cell.

A nanoparticle may, in some cases, emit an emission of radiation with one or more distinguishable peaks. One of ordinary skill in the art would understand a peak to refer to a local maximum in the intensity of the electromagnetic radiation, for example, when viewed as a plot of intensity as a function of wavelength. In some embodiments, a nanoparticle may emit electromagnetic radiation with a specific set of peaks. In some cases, a change in a stimulus may cause the nanoparticle to emit electromagnetic radiation including one or more peaks such that the peaks (e.g., the frequencies of the peaks, the intensity of the peaks) may be distinguishable from one or more peaks prior to the change in stimulus. In some cases, the change in a stimulus may cause the nanoparticle to emit electromagnetic radiation comprising one or more peaks such that peaks (e.g., the frequencies of the peaks, the intensity of the peaks) are distinguishable from the one or more peaks observed prior to the change in the stimulus. When the stimulus is the concentration of an analyte, the frequencies and/or intensities of the peaks may, in some instances, allow one to determine the analyte interacting with the nanoparticle by, for example, producing a signature that is unique to a particular analyte that is interacting with the nanoparticle. Determination of a specific analyte can be accomplished, for example, by comparing the properties of the peaks emitted in the presence of the analyte to a set of data (e.g., a library of peak data for a predetermined list of analytes).

A stimulus can include the pH of the organelle or cell. A change in the pH can be an increase or decrease in the pH.

A stimulus can include a modification of an analyte. For example, an analyte may be oxidized or reduced. In other examples, an analyte can be ionized. In another example, an analyte can include an ether, ester, acyl, or disulfide or other derivative.

A stimulus can include the concentration of an analyte. An analyte can include a reactive oxygen species, for example, hydrogen peroxide, superoxide, nitric oxide, and a peroxidase. Alternatively, an analyte can be carbon dioxide, adenosine triphosphate (ATP), nicotinamide adenine dinucleotide phosphate ($NADP^+$ or NADPH), or oxygen. In some instances, the concentration of the analyte may be relatively low (e.g., less than about 100 micromolar, less than about 10 micromolar, less than about 1 micromolar, less than about 100 nanomolar, less than about 10 nanomolar, less than about 1 nanomolar, or about a single molecule of the analyte). In some cases, the concentration of an analyte may be zero, indicating that no analyte is present.

Single walled carbon nanotubes are cylindrical sheets of graphene with extraordinary mechanical and electrical properties that have advanced the fields of electronics, materials, and sensors. See, Park, S., Vosguerichian, M. & Bao, Z. A review of fabrication and applications of carbon nanotube film-based flexible electronics. *Nanoscale* 5, 1727-52 (2013), Marconnet, A. M., Yamamoto, N., Panzer, M. a, Wardle, B. L. & Goodson, K. E. Thermal conduction in aligned carbon nanotube-polymer nanocomposites with high packing density. *ACS Nano* 5, 4818-25 (2011), Jacobs, C. B., Peairs, M. J. & Venton, B. J. Review: Carbon nanotube based electrochemical sensors for biomolecules. *Anal. Chim. Acta* 662, 105-27 (2010), and Sha, J. et al. Nanotubes complexed with DNA and proteins for resistive-pulse sensing. *ACS Nano* 7, 8857-69 (2013), each of which is incorporated by reference in its entirety. In particular, optical nanosensors have enabled the detection of analytes with high spatio-temporal resolution. See, Wang, Q. H. et al. Low dimensional carbon materials for applications in mass and energy transport. *Chem. Mater* 26, 172-183 (2014), and Landry, M. P. et al. Experimental tools to study molecular recognition within the nanoparticle corona. *Sensors (Basel).* 14, 16196-16211 (2014), each of which is incorporated by reference in its entirety. Semiconducting single walled carbon nanotubes (SWNT) are excellent signal transducers for nanosensors due to their fluorescence stability, lifetime, and emission in the near-infrared. See, Boghossian, A. a et al. Near-infrared fluorescent sensors based on single-walled carbon nanotubes for life sciences applications. *ChemSusChem* 4, 848-63 (2011), which is incorporated by reference in its entirety. Consequently, there has been much interest in developing nanosensors via noncovalent encapsulation of polymers with SWNT, such that the SWNT corona can recognize an analyte. See, Zhang, J. et al. Molecular recognition using corona phase complexes made of synthetic polymers adsorbed on carbon nanotubes. *Nat. Nanotechnol.* 8, 959-68 (2013), which is incorporated by reference in its entirety.

Single walled carbon nanotubes (SWNT) are well suited to act as single particle sensors in living organisms as they do not photobleach, and they fluoresce in the near infrared (NIR) in which tissues and biological samples are transparent. Proof of concept for optical detection of analytes in living biological tissues was recently demonstrated, in which a mixture of multiple chirality SWNT (HipCo, Unydim) allowed imaging of nitric oxide in extracted chloroplasts and leaves of living plants. See, Giraldo, J. et al. Plant nanobionics approach to augment photosynthesis and biochemical sensing. *Nat. Mater.* 13, 400-408 (2014), which is incorporated by reference in its entirety. Colloidal SWNT with high zeta potential spontaneously penetrated the chloroplast lipid bilayers and assembled within the photosynthetic machinery. SWNT infiltrated through the leaf lamina into intracellular spaces and organelles, allowed monitoring of free radicals in plants in real time.

However, one challenge in using chemically responsive fluorescent probes of any kind is obtaining an absolute signal such that probe intensity can be used to calculate local presence of an analyte unambiguously. In analytical chemistry, such probes are often employed as ratiometric sensors in which one of two distinct fluorophores report an analyte-independent reference signal to which the sensing signal is scaled. See, Doussineau, T. et al. On the design of fluorescent ratiometric nanosensors. *Chemistry (Easton)*. 16, 10290-9 (2010), which is incorporated by reference in its entirety. To date, it has not been possible to generate a ratiometric sensor using carbon nanotubes because of difficulty in separating the nanotubes as distinct chiral species with characteristic emission wavelengths. The signal observed from optical nanosensors has been largely limited to the fluorescence response of a multi-chirality SWNT sample with multiple peaks of near infrared emission. See, Barone, P. W., Baik, S., Heller, D. a & Strano, M. S. Near-infrared optical sensors based on single-walled carbon nanotubes. *Nat. Mater.* 4, 86-92 (2005), Iverson, N. M. et al. In vivo biosensing via tissue-localizable near-infrared-fluorescent single-walled carbon nanotubes. *Nat. Nanotechnol.* 8, 873-80 (2013), Kruss, S. et al. Neurotransmitter detection using corona phase molecular recognition on fluorescent single-walled carbon nanotube sensors. *J. Am. Chem. Soc.* 136, 713-24 (2014), and Giraldo, J. et al. Plant nanobionics approach to augment photosynthesis and biochemical sensing. *Nat. Mater.* 13, 400-408 (2014), each of which is incorporated by reference in its entirety. Other studies have also produced multimodal sensors, in which the same SWNT wrapping generates distinct optical signals from different molecular interactions. See, Heller, D. A. et al. Multimodal optical sensing and analyte specificity using single-walled carbon nanotubes. *Nat. Nanotechnol.* 4, 114-120 (2009), which is incorporated by reference in its entirety.

However, there are numerous advantages in developing SWNT ratiometric sensors, particularly for analyte quantification in living systems, where interfering biomolecules are abundant. See, Iverson, N. M. et al. In vivo biosensing via tissue-localizable near-infrared-fluorescent single-walled carbon nanotubes. *Nat. Nanotechnol.* 8, 873-80 (2013), which is incorporated by reference in its entirety. Though a sensor may respond clearly to an analyte in vitro, it is often very difficult to limit the sensor response to the analyte of interest when the sensor is immersed into a complex and dynamic biological sample. One approach to optimizing sensor development relies on extensive screening of the sensor in the presence of possible interfering molecules. See, Zhang, J. et al. Molecular recognition using corona phase complexes made of synthetic polymers adsorbed on carbon nanotubes. *Nat. Nanotechnol.* 8, 959-68 (2013), and Kruss, S. et al. Neurotransmitter detection using corona phase molecular recognition on fluorescent single-walled carbon nanotube sensors. *J. Am. Chem. Soc.* 136, 713-24 (2014), each of which is incorporated by reference in its entirety. This approach is time intensive and is therefore a significant limitation in the development of optical sensors. The signal from a non-responsive reference chirality within a ratiometric sensor ensures that the observed response is a direct result of the analyte presence, and can greatly facilitate and expedite future development of selective optical sensors. Additionally, single chirality SWNT are brighter than multichirality SWNT mixtures, reaching six times higher photoluminescence on a per-mass basis. See, Antaris, A. L. et al. Ultra-low doses of chirality sorted (6,5) carbon nanotubes for simultaneous tumor imaging and photothermal therapy. *ACS Nano* 7, 3644-3652 (2013), which is incorporated by reference in its entirety.

SWNT-based optical sensors often lack specificity for their target analyte in the presence of interfering biochemical compounds, therefore their use as in vivo sensors has been limited. To solve this problem, a ratiometric SWNT sensor can be used to provide a chirality-dependent response to one or more analytes. This platform relies on coating two or more different SWNT chiralities with two or more different coatings, one for each chirality. This fluorescence response would create a unique SWNT spectral signature for each analyte, while incorporating a non-responsive reference signal, thus improving sensor specificity and functionality in living tissues.

Carbon nanotubes can be classified according to the geometrical arrangement of the carbon atoms on their surface. This spatial distribution of the carbon lattice is represented by a pair of indices (n,m). The numbers n and m indicate unit vectors pointing in a direction on the carbon lattice. When m is not zero, and n and m are different numbers, the carbon nanotubes are chiral. For example, (6,5) and (7,6) are chiralities of carbon nanotubes where n=6 and m=5 and n=7 and m=6, respectively. A sample of single chirality carbon nanotubes all contain the same combination of (n,m). A ratio sensor can be made of two or more carbon nanotubes with two or more distinct (n,m) chiralities. Other examples of single chirality carbon nanotubes include (8,4), (8,3), (7,5), (10,2), (9,4), (8,6) and any combination of (n,m). The chirality of carbon nanotubes can significantly affect their electronic and optical properties such as their electronic band gap and consequently their absorbance and emission spectra.

Disclosed herein is a ratiometric sensor composed of two individually encapsulated SWNT chiralities. 6,5 SWNT is encapsulated by one coating, that forms a non-responsive sensor to a particular analyte. 7,6 chirality SWNT is encapsulated by another coating, that produces a responsive sensor to that same analyte. When combined together, the individually encapsulated 6,5 and 7,6 SWNT form a ratiometric sensor that can be delivered into plant leaves and enable selective ratiometric sensing of plant free radicals and pollutants NO and $H_2O_2$. Using a method for rapid and efficient coating exchange of single chirality SDS-SWNT, the first SWNT ratiometric sensor was synthesized with 6,5 and 7,6 chiralities coated with single stranded DNA and Polyvinyl alcohol. These ratiometric platforms were designed for monitoring 7,6 SWNT NIR fluorescence quenching in the presence of the free radical analytes while the 6,5 SWNT chirality is unresponsive to free radical analytes. A multimodal NIR spectral signature increases SWNT sensor selectivity to biochemicals generated by plants or pollutants in the environment. Spatial and temporal patterns of the ratio sensor NIR fluorescence in the leaf lamina in response to nitric oxide and hydrogen peroxide were monitored in vitro and imaged in vivo in real time. This nanobionic approach of interfacing nanoparticles with leaves can lead to the development of cost effective, selective, and stable plant biochemical detectors.

In a ratiometric sensor composed of two individually encapsulated SWNT chiralities, a first plurality of nanoparticles can have a first chirality, and a second plurality of nanoparticles can have a second chirality. In one embodiment, the first plurality of nanoparticles with the first chirality can respond to the analyte while the second plurality of nanoparticles with the second chirality cannot respond to the analyte at all. In this case, the second plurality of nanoparticles with the second chirality is the internal control for the signal intensity. In another embodiment, both the first plurality of nanoparticles with the first chirality and the second plurality of nanoparticles with the second chirality can respond to the same analyte but show different signal intensities and wavelength profiles in emission spectra. The larger the difference between the signal intensities of the two chirality nanotubes, the closer the two emissions peak wavelengths can be. In other words, the emission profiles of two different chirality nanotubes can be close to each other but without overlap that can interfere with ability to detect a signal. For example, the difference in the wavelengths of 6,5 and 7,6 chirality SWNT is 150 nm and the intensities of signal of the two chirality SWNT shows 20% difference.

A ratiometric sensor can be composed of a single chirality of nanotube, two chiralities of nanotubes, three chiralities of nanotube or more.

The advantages of SWNT ratiometric sensing are numerous, particularly for in vivo applications. Sensor selectivity is a common obstacle to the application of sensors in living systems, where interfering biomolecules are abundant. See, Iverson, N. M. et al. In vivo biosensing via tissue-localizable near-infrared-fluorescent single-walled carbon nanotubes. *Nat. Nanotechnol.* 8, 873-80 (2013), which is incorporated by reference in its entirety. Though a sensor may respond clearly to an analyte in vitro, it is often very difficult to achieve selectivity for the analyte when the sensor is immersed into a biological sample. One approach to optimize sensor selectivity relies on extensive screening of the sensor in the presence of possible interfering molecules. See, Kruss, S. et al. Neurotransmitter detection using corona phase molecular recognition on fluorescent single-walled carbon nanotube sensors. *J. Am. Chem. Soc.* 136, 713-24 (2014), and Zhang, J. et al. Molecular recognition using corona phase complexes made of synthetic polymers adsorbed on carbon nanotubes. *Nat. Nanotechnol.* 8, 959-68 (2013), each of which is incorporated by reference in its entirety. However, this approach is time intensive and a significant limitation in the development of optical sensors. The signal from a non-responsive reference chirality within a ratiometric sensor ensures that the observed signal is a direct result of an analyte presence, and can greatly facilitate and expedite future development of selective optical sensors. Furthermore, biocompatible single chirality SWNT have been shown to be brighter, reaching six times higher photoluminescence on the per mass basis. See, Antaris, A. L. et al. Ultra-low doses of chirality sorted (6,5) carbon nanotubes for simultaneous tumor imaging and photothermal therapy. ACS Nano 7, 3644-3652 (2013), which is incorporated by reference in its entirety.

One drawback of using single chirality SWNT suspended in sodium dodecyl sulfate (SDS) is that large scale separation through columns of sephacryll followed by coating exchange of SDS with other polymers by dialysis is a labor-intensive process. See, Liu, H., Nishide, D., Tanaka, T. & Kataura, H. Large-scale single-chirality separation of single-wall carbon nanotubes by simple gel chromatography. *Nat. Commun.* 2, 1-8 (2011), which is incorporated by reference in its entirety. Manual separation of large volumes of single chirality SWNT in sephacryll columns can take several days. Similarly, coating exchange by dialysis is slow requiring numerous changes of water baths over 24 to 32 hours, generally has low percent SWNT recovery, and therefore is not optimal for SWNT suspensions at low concentrations. Recently, automated and scalable chromatographic SWNT separation protocols have allowed routine suspensions of high purity single chirality SWNT in SDS. See, Flavel, B. S., Moore, K. E., Pfohl, M., Kappes, M. M. & Hennrich, F. Separation of single-walled carbon nanotubes with a gel permeation chromatography system. *ACS Nano* 8, 1817-1826 (2014), which is incorporated by reference in its entirety. However, polymer coating exchange processes for SDS-SWNT remains a bottleneck for high throughput development of single chirality SWNT biocompatible sensors. Here, an automatic single chirality separation was combined with a novel, rapid, and efficient coating exchange method for SWNT separated in SDS. A quantitative theory of adsorptive separation was applied for electronic sorting of SWNT of (6,5) and (7,6) chiralities. See, Jain, R. M., Tvrdy, K., Han, R., Ulissi, Z. & Strano, M. S. Quantitative theory of adsorptive separation for the electronic sorting of single-walled carbon nanotubes. *ACS Nano* 8, 3367-79 (2014), which is incorporated by reference in its entirety. This high throughput protocol enabled better yields and low cost suspension of single chirality SWNT sensors for biological research and commercial applications.

Another limitation for the production of ratiometric sensors is the inherent difficulty in exchanging SWNT coronas. To produce a ratiometric sensor, one must selectively wrap one SWNT chirality with a corona that is responsive to the analyte, and another SWNT chirality with a corona that is either non-responsive or responds opposite to the analyte signal. The difficulty lies in exchanging one SWNT corona, SDS in this case, for a corona that will enable a selective response to the target analyte with high exchange efficiency. As such, large-volume polymer coating exchange processes for SDS-SWNT remains a bottleneck for high throughput development of single chirality SWNT sensors. The ability to separate single walled carbon nanotubes in scalable quantities combined with a novel, rapid, and efficient SWNT corona exchange method (RACES), enables the production of ratiometric sensors to detect separate analytes using a single optical sensing platform.

A ratiometric sensor with SWNT can be localized in any living tissue or in a living organism. Functionalized SWNT localized inside leaf sections enable real-time ratiometric detection and imaging of nitric oxide and hydrogen peroxide, whereby the functionalized SWNT act as as photostable nanosensors. To accomplish this goal (1) a method for rapid and efficient coating exchange of single chirality SWNT was developed; (2) the first ratiometric SWNT sensor was synthesized for in vitro and in vivo sensing of free radicals; (3) a two channel NIR imaging technique was used to image the fluorescence emission of single chirality SWNT in real-time, in vivo in leaf tissues.

To create two distinct examples of ratiometric sensors, one for $H_2O_2$ and the other for NO, unique corona phases that are selective to each analyte were identified and paired with a corona phase that is largely invariant to that analyte by using RACES. The result, for each case, is a pair of SWNT emitters, where only one is modulated in response to an analyte and the other signal acts as a reference, allowing absolute calibration independent of overall intensity, a clear advance from a ratiometric approach. This ratiometric sensor can be utilized in vivo by detecting $H_2O_2$ and NO in living plant tissues.

Suspension and Characterization of Poly-Coated Single Chirality SWNT

Figure 1B:
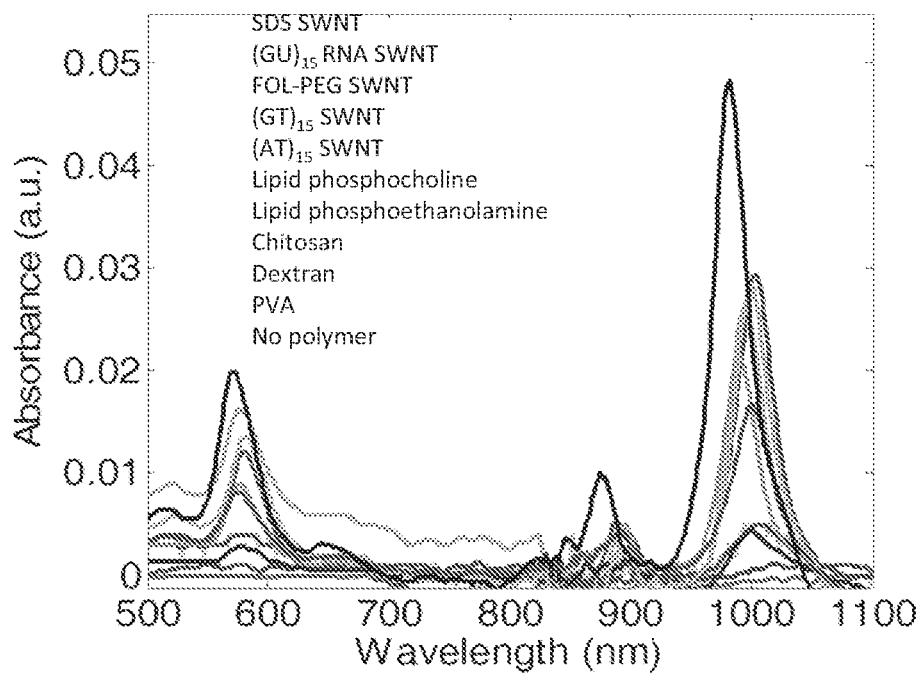
Figure 1C:
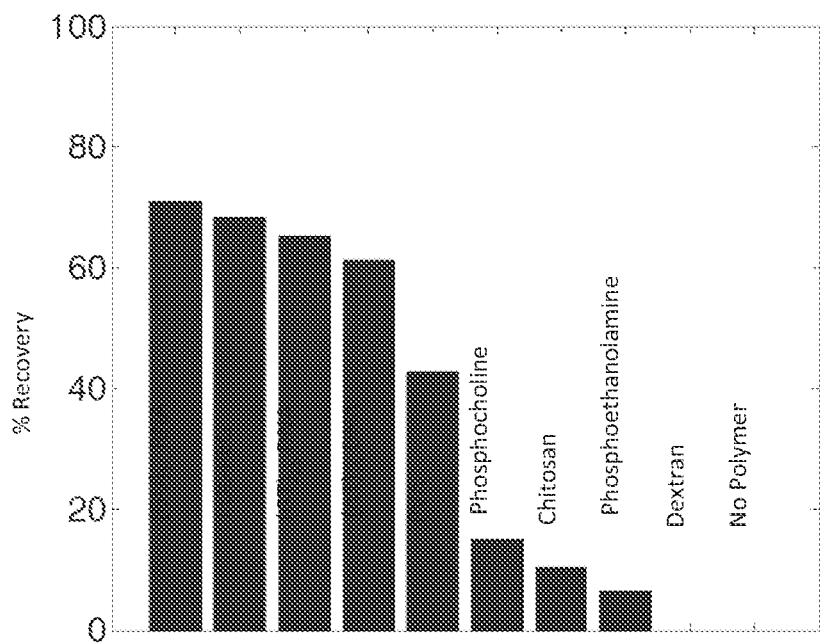

A technique for coating exchange of SDS single chirality SWNT allows rapid and efficient suspension of single chirality SWNT with a variety of polymers. After SWNT separation by chirality in 5% SDS, the polymer is added to the suspension of carbon nanotubes at a 10:1 mass ratio. During bath sonication, the methanol content of the mixture is increased via dropwise MeOH addition to more than 60% v/v. Increasing the MeOH concentration beyond the critical micelle concentration for SDS (from 8.27 mM to 10.9 mM) prevents the formation of SDS micelles in solution, thereby removing the SDS from the SWNT surface as the polymer encapsulates the SWNT (FIG. 1A). The result is a gradual and simultaneous SDS desorption and polymer adsorption to the carbon nanotube surface. The protocol can be performed in a few hours with yields up to ~71% depending on the chemical structure of the polymer (FIGS. 1B and 1C).

Figure 2:
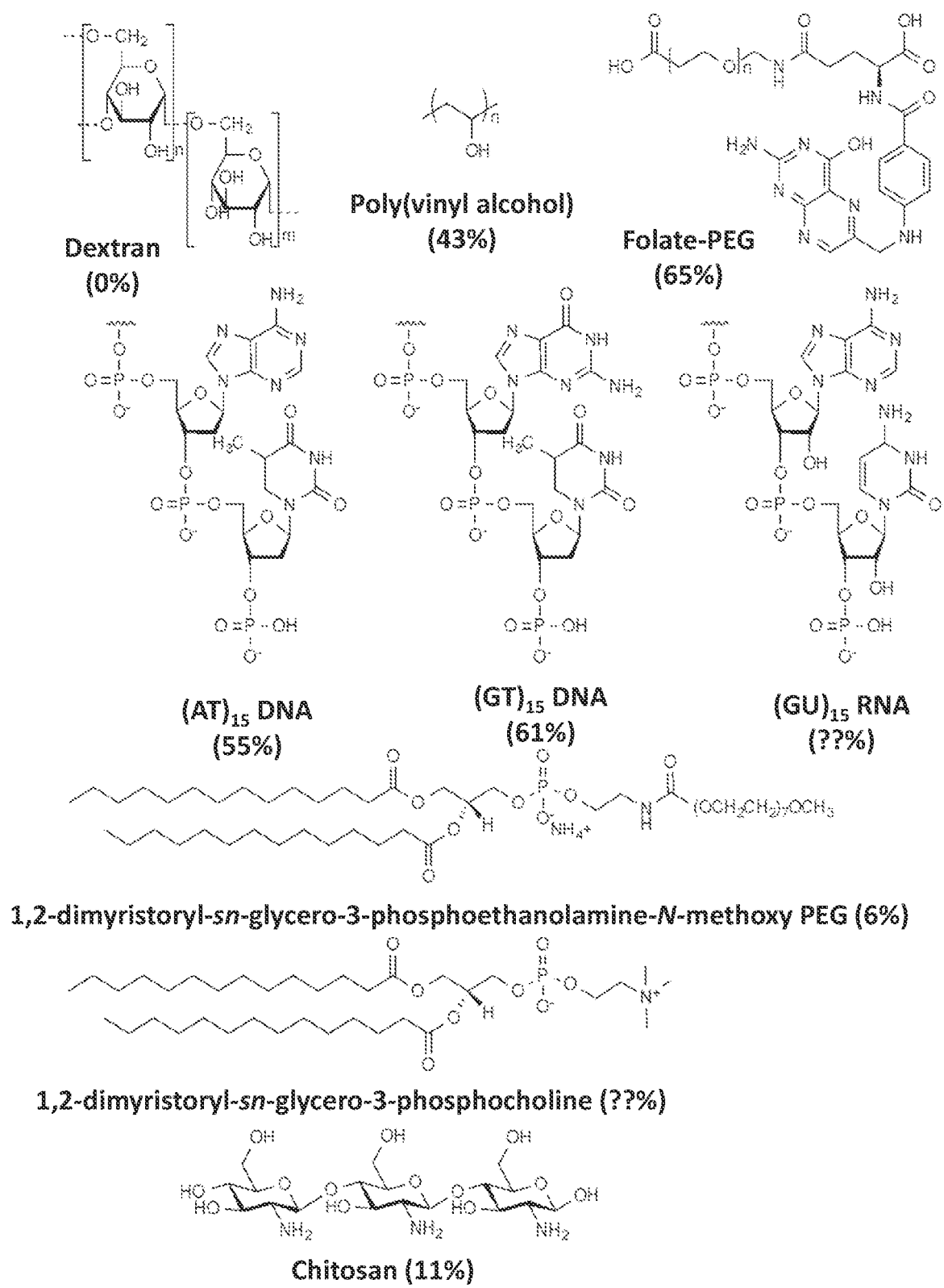
FIG. 2 shows chemical structures of polymers used for single chirality SWNT coating exchange.

The efficiency of the SWNT coating exchange can be dependent on the binding affinity of the polymer to the SWNT surface. Exchange recovery depends on the chemical structure of the polymer, where increased exchange recovery is correlated to increased aromaticity in the polymer into which SWNT are being exchanged. Herein, DNA, RNA, and FOL-PEG enable more efficient SWNT coating exchange. Polymers high in chemical moieties that are likely to bind to the SWNT surface via Pi stacking interactions, such as phenol rings, result in high-yield coating exchanges. The exchange efficiency was tested for a variety of different polymers as depicted in (FIG. 2). The exchange efficiency was determined by the percent recovery of SWNT, as calculated by comparing initial and final concentrations of SWNT based on the E11 peak of absorbance for 6,5 SWNT. As expected, the highest exchange efficiency in DNA (69%), RNA (71%), and FOL-PEG (65%) coatings, which are rich in aromatic groups (FIGS. 1B and 1C). In contrast, this exchange protocol has very low SWNT recovery when SDS is exchanged with lipids such as phosphocoline (15%) and phosphoethanolamine (6.4%), due to the low binding affinity of these polymers to the SWNT.

SWNT Ratiometric Detection of Free Radicals In Vitro

Figure 3A:
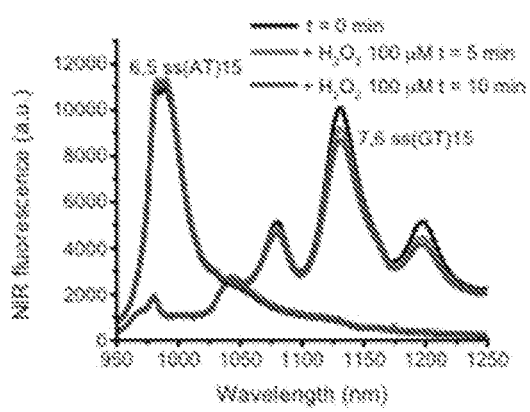
FIGS. 3A-3D are graphs showing ratiometric sensor response to hydrogen peroxide (FIGS. 3A and 3C) and nitric oxide (FIGS. 3B and 3D) in vitro. The graphs show the changes in the near infrared fluorescence spectrum of a, 6,5 $ss(AT)_{15}$ and 7,6 $ss(GT)_{15}$ SWNT to hydrogen peroxide (FIG. 3A), and 6,5 PVA and 7,6 $ss(GT)_{15}$ SWNT to nitric oxide (FIG. 3B), NIR response in a SWNT ratiometric sensor platform to $H_2O_2$ (FIG. 3C) and NO (FIG. 3D).
Figure 3B:
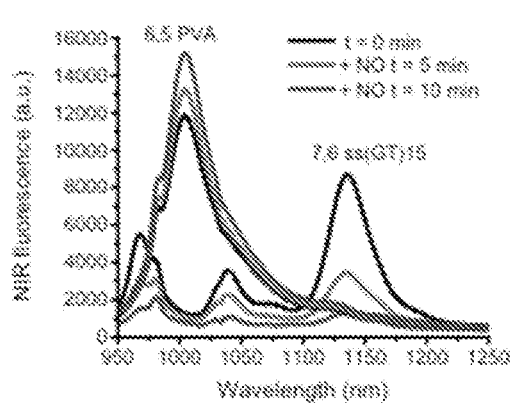
Figure 3C:
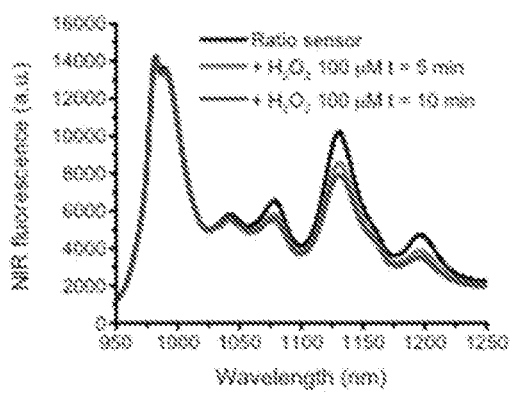
Figure 3D:
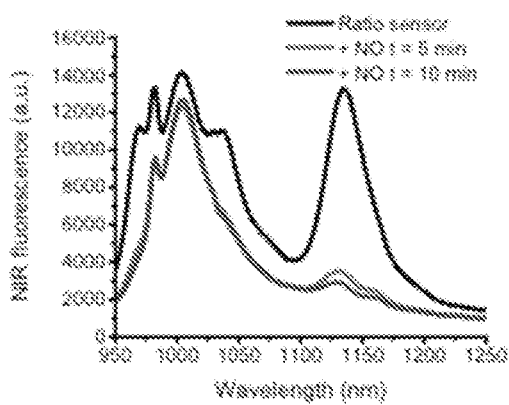
Figure 4A:
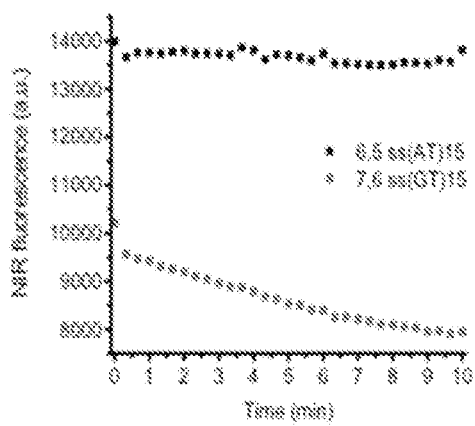
FIGS. 4A-4D show temporal changes in SWNT peak intensity and ratio of intensity (R) after addition of hydrogen peroxide and nitric oxide.
Figure 4B:
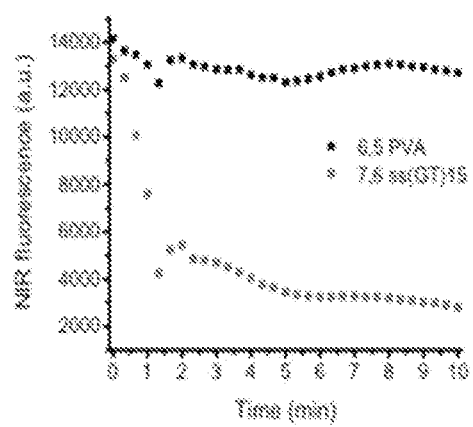

Coating single chirality SWNT with polymers of different moieties can enable the production of a ratiometric platform that can report on the presence of free radical target analytes while remaining insensitive to common signal interfering factors such as but not limited to: dilution effects, the local nanoparticle concentration, and SWNT response to other biomolecules. Two different analytical problems were selected to address using this ratiometric detection approach. In the first, $ss(GT)_{15}$ DNA wrapped 7,6 SWNT (Em=1130 nm) that quenches in the presence of $H_2O_2$, was combined with 6,5 $ss(AT)_{15}$ DNA SWNT (Em=985 nm) which were largely invariant to $H_2O_2$. The result is a pair of emission wavelengths that can yield changes in $H_2O_2$ independent of absolute intensity. The response of a ratiometric sensor to hydrogen peroxide was tested. Hydrogen peroxide is a reactive oxygen species generated by the plant photosynthetic pigments under bright light. The changes in 6,5 $ss(AT1)_{15}$ and 7,6 $ss(GT)_{is}$ fluorescence to hydrogen peroxide was tested. The NIR fluorescence of 6,5 SWNT coated with $ss(AT)_{is}$ was not affected by the presence of 100 μM $H_2O_2$ (FIG. 3A). In contrast, 7,6 $ss(GT)_{is}$ SWNT fluorescence quenched by ~20% ten minutes after the addition of 100 μM $H_2O_2$ (FIGS. 3A and 4A). The changes in NIR fluorescence were similar when the single chirality SWNT were tested independently with $H_2O_2$ in vitro (FIG. 3A) and combined in a ratiometric platform (FIG. 3C). For NO sensing, $ss(GT)_{15}$ DNA wrapped 7,6 (Em=1130 nm) SWNT was mixed with 6,5 $ss(AT)_{15}$ PVA SWNT (Em=1005 nm) (FIG. 3B). Combined in a ratiometric platform, the NIR fluorescence of 6,5 PVA SWNT did not quench in the presence of 500 μM NO while 7,6 $ss(GT)_{15}$ SWNT exhibited a strong decrease in NIR fluorescence (FIG. 3D). The largest NIR response of 7,6 $ss(GT)_{15}$ SWNT occurred a few minutes after the addition of NO (FIG. 4B). Similarly, the NIR fluorescence of 6,5 PVA SWNT did not quench in the presence of 50 μM nitric oxide while 7,6 $ss(GT)_{15}$ SWNT exhibited a strong reduction in NIR fluorescence only a few minutes after addition of 50 μM NO (FIG. 4B). This free radical has been previously shown to dramatically reduce the NIR fluorescence of a mix of $ss(AT)_{15}$ SWNT (Unydim) both in vitro and more recently in leaves of living plants in vivo. See, Giraldo, J. et al. Plant nanobionics approach to augment photosynthesis and biochemical sensing. *Nat. Mater.* 13, 400-408 (2014), which is incorporated by reference in its entirety. PVA appears to be among very few polymers able to prevent the interaction of NO with the carbon nanotube surface. See, Zhang, J. et al. Single molecule detection of nitric oxide enabled by $d(AT)_{15}$ DNA adsorbed to near infrared fluorescent single-walled carbon nanotubes. *J. Am. Chem. Soc.* 133, 567-581 (2011), which is incorporated by reference in its entirety. The response of 6,5 PVA SWNT to NO tends to be an increase in fluorescence. In a ratiometric platform with 7,6 $ss(GT)_{15}$, the 6,5 PVA SWNT showed an insignificant decline in fluorescence. These results demonstrate for the first time that ratiometric detection of free radicals using SWNT is possible. By coating single chirality SWNT with polymers of different moieties, a ratiometric platform that can report on the presence of target analytes was built while remaining insensitive to signal interfering factors such as dilution effects, the local nanoparticle concentration, and SWNT response to other biomolecules. This platform can lead to more selective SWNT based sensors as each chirality coated with a different polymer can create a unique spectral signature in response to an analyte. This platform can be expanded to the use of multiple SWNT chiralities, where each chirality can be functionalized with a unique moiety. This approach can dramatically improve the selectivity of SWNT sensing platforms, particularly in non-homogenous and chemically complex living tissues, or can enable the concurrent detection of multiple analytes.

Figure 4C:
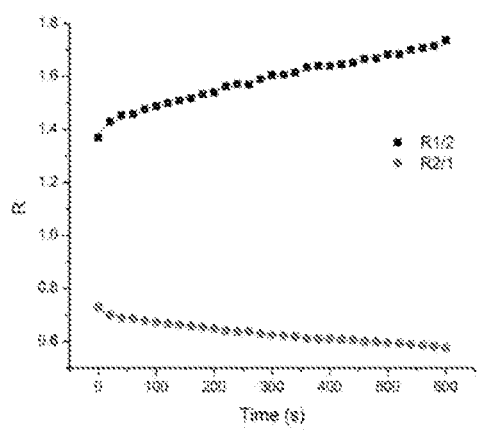
Figure 4D:
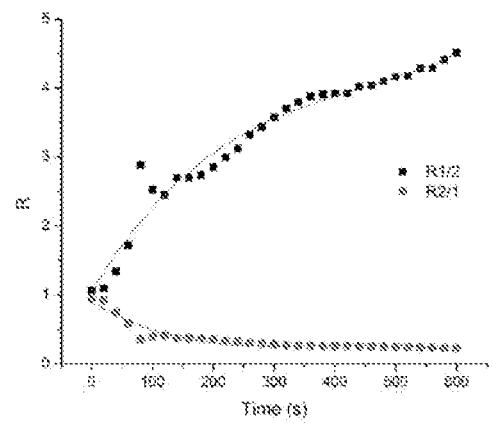

With a method analogous to that used for visible dye based ratiometric systems (see, Pomorski, A. & Kochańczyk, T. Method for accurate determination of dissociation constants of optical ratiometric Systems: chemical probes, genetically encoded sensors, and interacting molecules. *Anal. Chem.* 85, 11479-11486 (2013), which is incoroporated by reference in its entirety), the change of ratio of intensity (R) was calculated over time (FIGS. 4C and 4D). R response was determined as the normalized signal difference between the 6,5 chirality and the 7,6 chirality.

$$R(t) = \frac{I_{6,5}^{norm}(t)}{I_{7,6}^{norm}(t)} \tag{1}$$

Where, $$I_{6,5}^{norm}(t) = \frac{I_{6,5}(t)}{I_{6,5}(0)} \quad (2)$$

And, $$I_{7,6}^{norm}(t) = \frac{I_{7,6}(t)}{I_{7,6}(0)} \quad (3)$$

Two ratios were analyzed, R1/2 and R2/1, where R1 represents the NIR intensity of the 6,5 chirality and R2 the NIR intensity of the 7,6 chirality. $H_2O_2$ and NO were used the evaluate the selectivity of 6,5 ss(AT)$_{15}$ and 7,6 ss(GT)$_{15}$ SWNTs. Only the 7,6 ss(GT)$_{15}$ SWNT shows selective changes in fluorescence (at 1130 nm) in response to addition of $H_2O_2$ and NO. The linear response of 7,6 ss(GT)$_{15}$ SWNT to addition of $H_2O_2$ suggests a constant binding (or dissociation) affinity. FIG. 4C exhibits the dependence of the intensity ratios of absorbance for $I_{6,5}^{norm}(t)$ at 984 nm to that of $I_{7,6}^{norm}(t)$ at 1131 nm on time for $H_2O_2$. R(t) values were observed to increase monotonically from t=0 to t=600 s. The non-monoatomic nature of R1/2($I_{6,5\ (960\ nm)}/I_{7,6\ (1130\ nm)}$ and R2/1 ($I_{7,6\ (1130\ nm)})/I_{6,5\ (960\ nm)}$) for NO at short times could be due to some reversibility of ligand binding (fitting coefficients can be found in FIGS. 9A and 9B). The linear behavior of the $H_2O_2$ ratiometric sensor beyond t=20 s can be attributed to the fact that the binding sites of SWNTs are still unsaturated at the relatively low peroxide concentrations utilized, which implies that the binding probabilities are unchanging. The intensity ratios of $I_{6,5}^{norm}(t)$ at 1004 nm to that of $I_{6,5}^{norm}(t)$ at 1135 nm on time for NO are similarly shown in FIG. 4D. R(t) values were observed to increase with time from t=0 to t=600 s. The observed non-monoatomic nature of R for NO at short times (t<120 s) could be due to some reversibility of ligand binding. These results indicate that the ratiometric absorbance change could successfully read out the binding of $H_2O_2$ or NO on 6,5 ss(AT)$_{15}$ and 7,6 ss(GT)$_{15}$ SWNT in practical applications.

Spatial and Temporal Patterns of Ratiometric Sensor Photoluminescence in Living Tissues A eukaryotic cell is a cell that contains membrane-bound organelles, most notably a nucleus. An organelle is a specialized subunit within a cell that has a specific function, and can be separately enclosed within its own lipid bilayer. Examples of organelles include mitochondria, chloroplasts, Golgi apparatus, endoplasmic reticulum, and as previously mentioned, the nucleus. Organelles are found within the cell cytoplasm, an intracellular fluid that is separated from extracellular fluid by the plasma membrane. The plasma membrane is a double layer (i.e., a bilayer) of phospholipids that permits only certain substances to move in and out of the cell.

In addition to these features, plant cells include specialized organelles that are not generally found in animal cells. For example, plant cells include a rigid cell wall. Plant cells also include chloroplasts. Chloroplasts are chlorophyll-containing double-membrane bound organelles that perform photosynthesis. Chloroplasts are believed to be descendants of prokaryotic cells (e.g., cyanobacteria) that were engulfed by a eukaryotic cell.

Dyes with fluorescence in visible wavelengths have been commonly used as sensors for $H_2O_2$ and NO. See, Rhee, S. G., Chang, T.-S., Jeong, W. & Kang, D. Methods for detection and measurement of hydrogen peroxide inside and outside of cells. *Mol. Cells* 29, 539-49 (2010), Miller, E. W. & Chang, C. J. Fluorescent probes for nitric oxide and hydrogen peroxide in cell signaling. *Curr. Opin. Chem. Biol.* 11, 620-5 (2007), Foissner, I., Wendehenne, D., Langebartels, C. & Durner, J. In vivo imaging of an elicitor-induced nitric oxide burst in tobacco. *The Plant journall* 23, 817-24 (2000), and Lim, M. H., Xu, D. & Lippard, S. J. Visualization of nitric oxide in living cells by a copper-based fluorescent probe. *Nat. Chem. Biol.* 2, 375-80 (2006), each of which is incorporated by reference in its entirety. Although these fluorophores enable imaging with cellular resolution, in real time, they present a set of complex problems for in vivo applications. See, Swanson, S. J., Choi, W.-G., Chanoca, A. & Gilroy, S. In vivo imaging of Ca2+, pH, and reactive oxygen species using fluorescent probes in plants. *Annu. Rev. Plant Biol.* 62, 273-97 (2011), and Zhang, X. et al. Interfering with nitric oxide measurements: 4,5-diaminofluorescein reacts with dehydroascorbic acid and ascorbic acid. *J. Biol. Chem.* 277, 48472-8 (2002), each of which is incorporated by reference in its entirety. Amplex red is widely used for imaging low concentrations of $H_2O_2$ but has been rarely shown to work in living tissues due to its photodegradation. See, Driever, S. M., Fryer, M. J., Mullineaux, P. M. & Baker, N. R. in *Plant signal Transduct.* (Pfannschmidt, T.) 479, 109-116 (Humana Press, 2009), which is incorporated by reference in its entirety. The membrane permeable $H_2DCF$-DA dye has been used to detect $H_2O_2$ in living organisms despite its relatively non-selectivity to reactive oxygen species (ROS) and susceptibility to photo-oxidation and photobleaching. See, Zulfugarov, I. S., Tovuu, A., Kim, J.-H. & Lee, C.-H. Detection of reactive oxygen species in higher plants. *J. Plant Biol.* 54, 351-357 (2011), and Swanson, S. J., Choi, W.-G., Chanoca, A. & Gilroy, S. In vivo imaging of Ca2+, pH, and reactive oxygen species using fluorescent probes in plants. *Annu. Rev. Plant Biol.* 62, 273-97 (2011), each of which is incorporated by reference in its entirety. Imaging of NO in living systems has been performed with diamionofluoresceins with the disadvantage that their fluorescein chromophore is responsive to changes in pH[31] and reacts with dehydroascorbic and ascorbic acid. See, Zhang, X. et al. Interfering with nitric oxide measurements: 4,5-diaminofluorescein reacts with dehydroascorbic acid and ascorbic acid. *J. Biol. Chem.* 277, 48472-8 (2002), which is incorporated by reference in its entirety.

Plants are optically dense living organisms due to thick tissues and photosynthetic pigments, making it difficult to detect analytes in vivo. $H_2O_2$ can be generated in plants by the leaf photosynthetic pigments while NO can be produced by multiple metabolic pathways. See, Arora, A., Sairam, R. & Srivastava, G. Oxidative stress and antioxidative system in plants. *Curr. Sci* 82, 1227-1238 (2002), and Besson-Bard, A., Pugin, A. & Wendehenne, D. New insights into nitric oxide signaling in plants. *Annu. Rev. Plant Biol.* 59, 21-39 (2008), each of which is incorporated by reference in its entirety. SWNT are well suited for in vivo detection of trace levels of chemical compounds with short lifetimes such as $H_2O_2$ and NO in plants. SWNT photoluminesce in the NIR in which living tissues are relatively transparent, do not photobleach, and allow detection at the single particle level. See, Giraldo, J. et al. Plant nanobionics approach to augment photosynthesis and biochemical sensing. *Nat. Mater.* 13, 400-408 (2014), and Zhang, J. et al. Single molecule detection of nitric oxide enabled by d(AT)15 DNA adsorbed to near infrared fluorescent single-walled carbon nanotubes. *J.*

Am. Chem. Soc. 133, 567-581 (2011), each of which is incorporated by reference in its entirety.

The response of two distinct ratiometric sensors was tested in real-time, inside sections of leaves of living plants. The NIR response of the 6,5 PVA and 7,6 ss(GT)$_{15}$ SWNT ratio sensor for hydrogen peroxide and that of 6,5 (GT)$_{15}$ DNA and 7,6 (AT)$_{15}$ DNA-SWNT ratio sensor for NO. The SWNT comprising each ratio sensors were delivered inside cross sections of leaves mounted on a microfluidic perfusion platform, as described in herein. Leaf sections were washed with PBS buffer to remove free SWNT not-incorporated into the leaf sections.

Figure 5A:
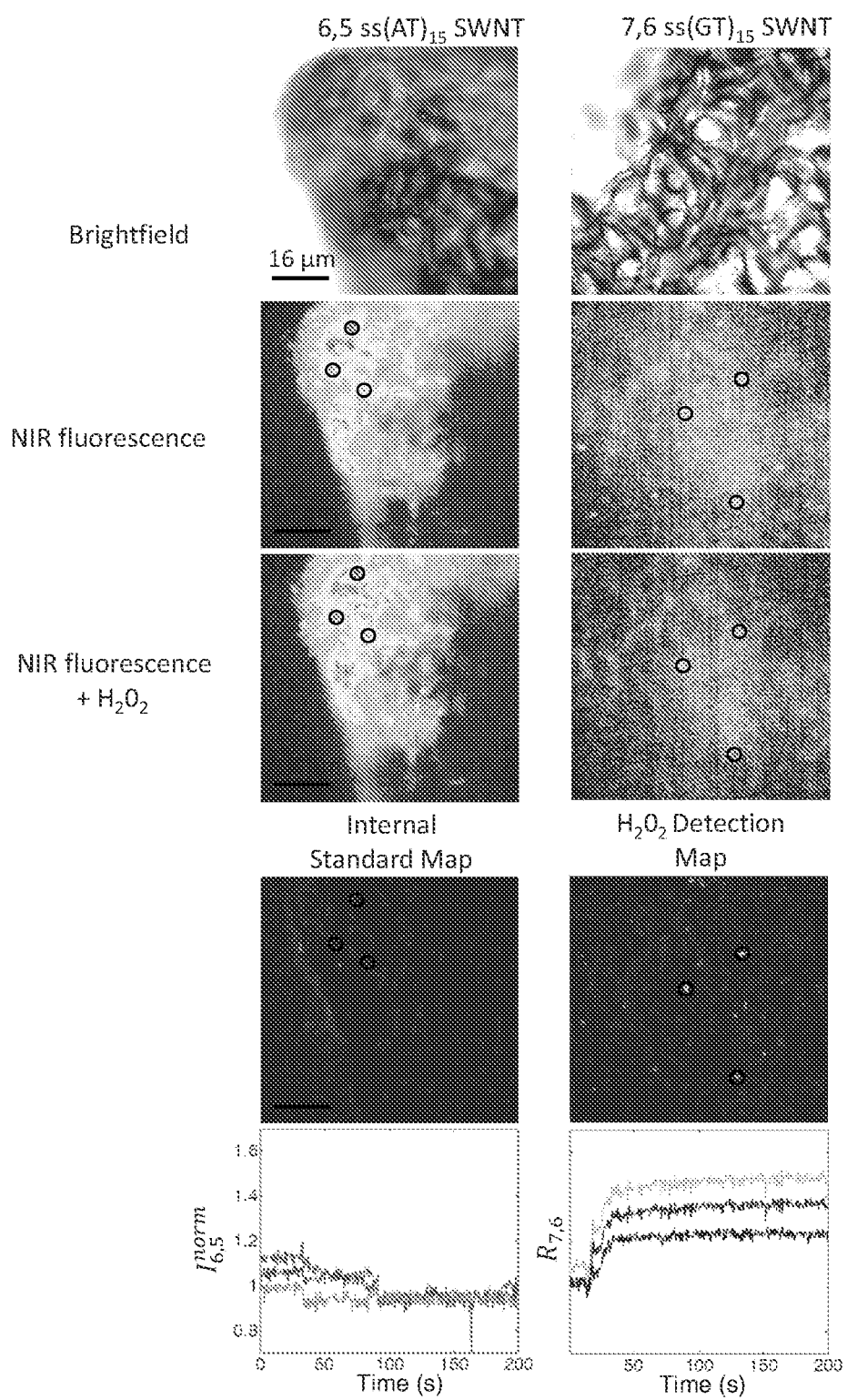
FIGS. 5A-5B show ratiometric sensor responses to hydrogen peroxide in vivo inside leaves.
Figure 5B:
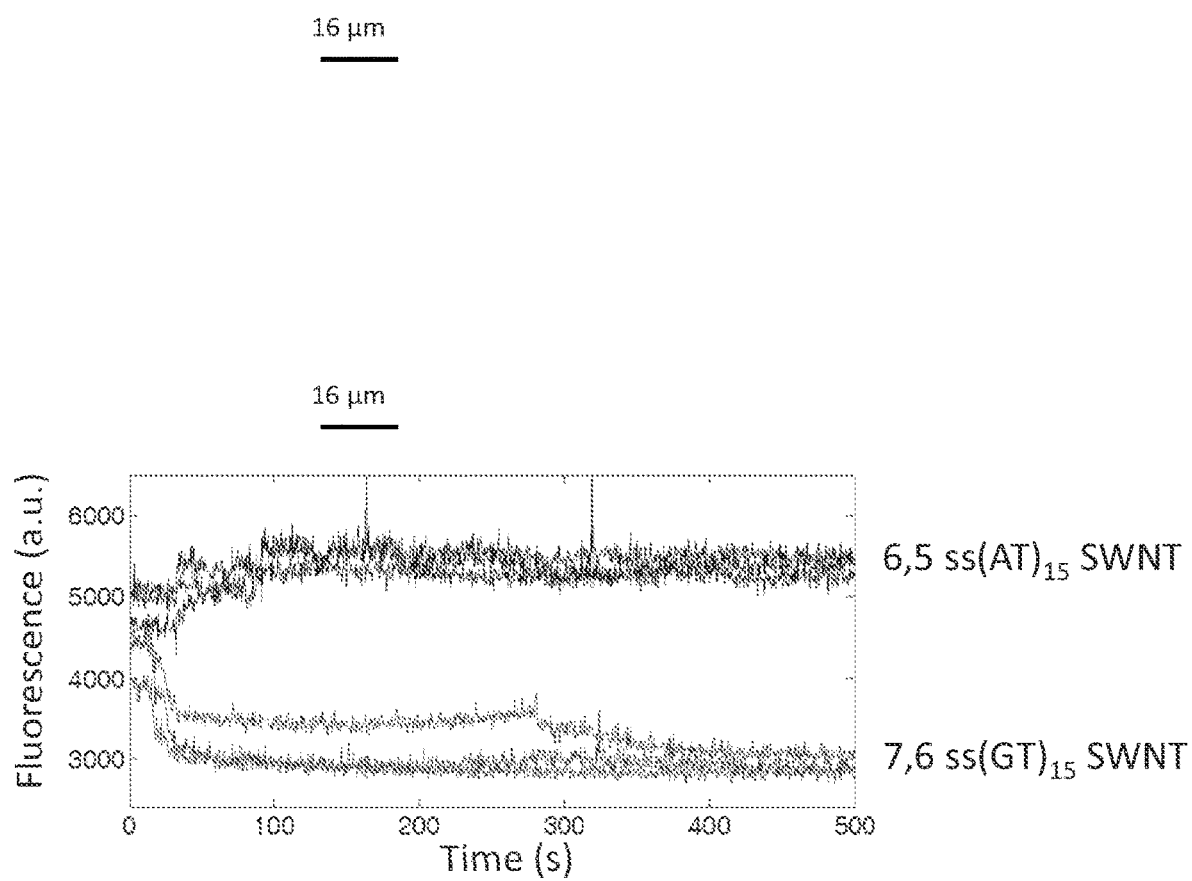
Figure 6A:
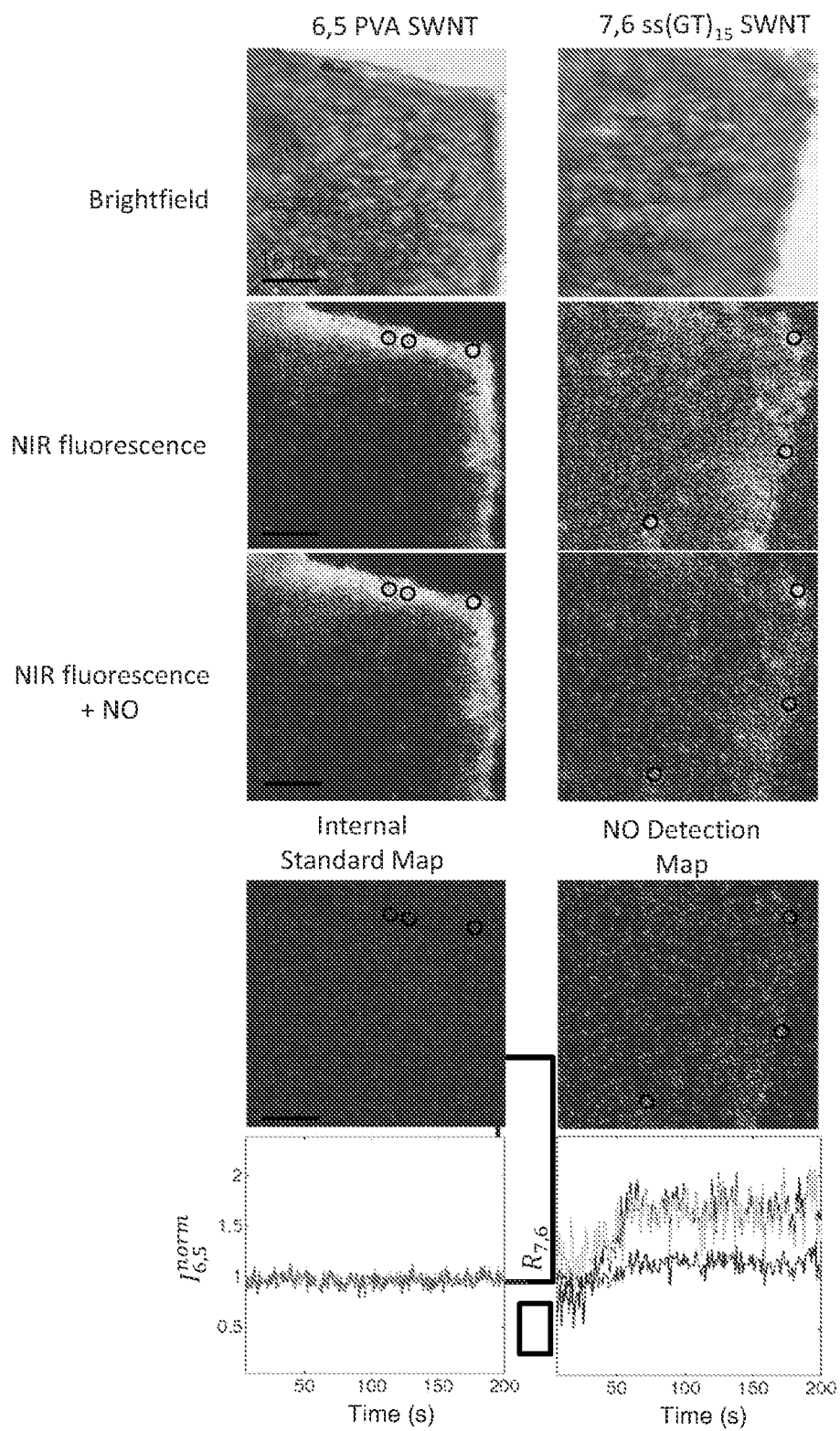
FIGS. 6A-6B show ratiometric sensor responses to nitric oxide in vivo inside leaves.

Upon exposure to $H_2O_2$, The 6,5 ss(AT)$_{15}$ SWNT NIR fluorescence slightly increased by ~11% while the 7,6 ss(GT)15 SWNT quenched by nearly 40% in the presence of $H_2O_2$ (FIG. 5A). The changes in NIR fluorescence of the 6,5 and 7,6 SWNT occurred rapidly in less than 50 s after the addition of this reactive oxygen species (FIG. 5B). Similarly, NO in solution induced no response in 6,5 SWNT but led to a decrease in NIR fluorescence of the 7,6 ss(GT)$_{15}$ SWNT of 50% (FIG. 6A). The changes in SWNT photoluminescence of 7,6 ss(GT)$_{15}$ SWNT were recorded after less than 50 s after exposure to NO.

Figure 8A:
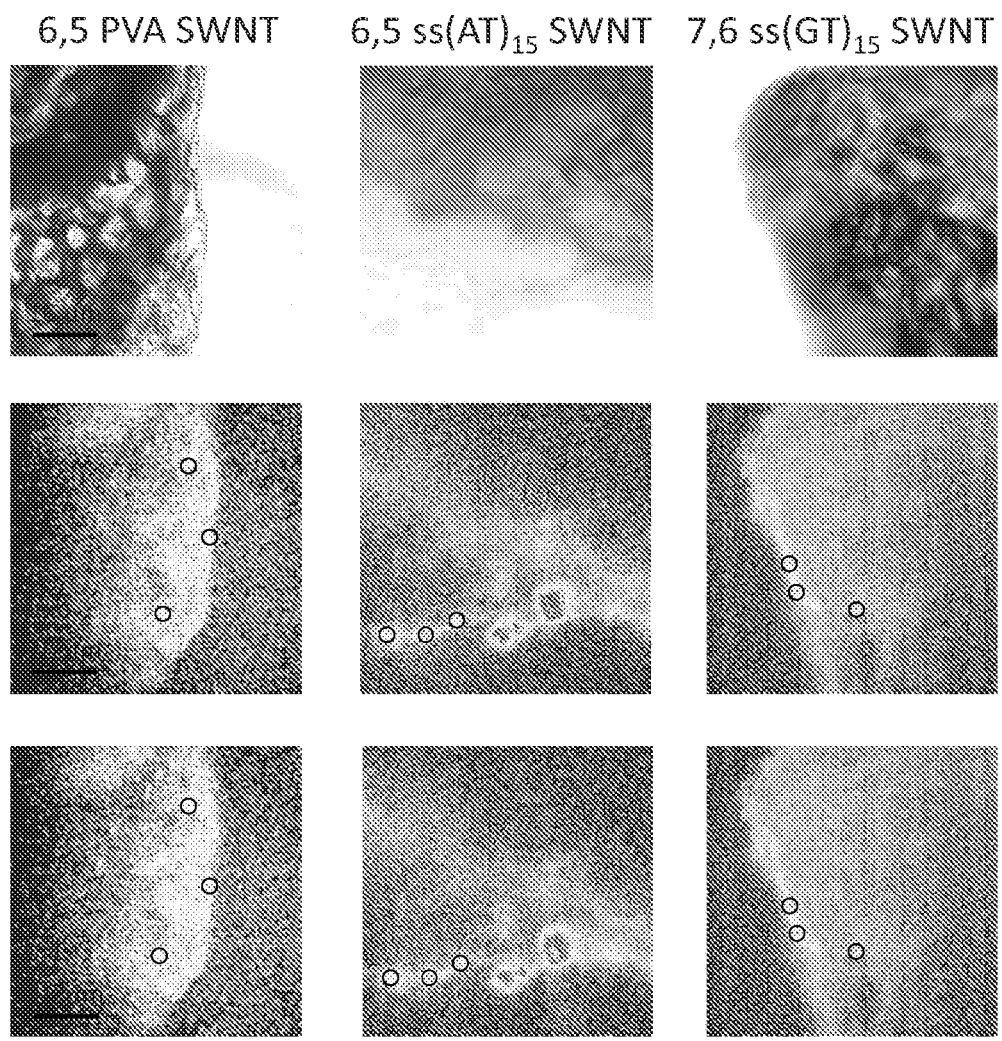
FIGS. 8A-8B show cross section time series of ratiometric sensor responses to water in vivo inside leaves. Trace analysis of 6,5 PVA, 6,5 $ss(AT)_{15}$, and 7,6 $ss(GT)_{15}$ peak intensity changes over time upon addition of water, for a leaf section infiltrated with ratiometric sensors for $H_2O_2$ and NO.
Figure 8B:
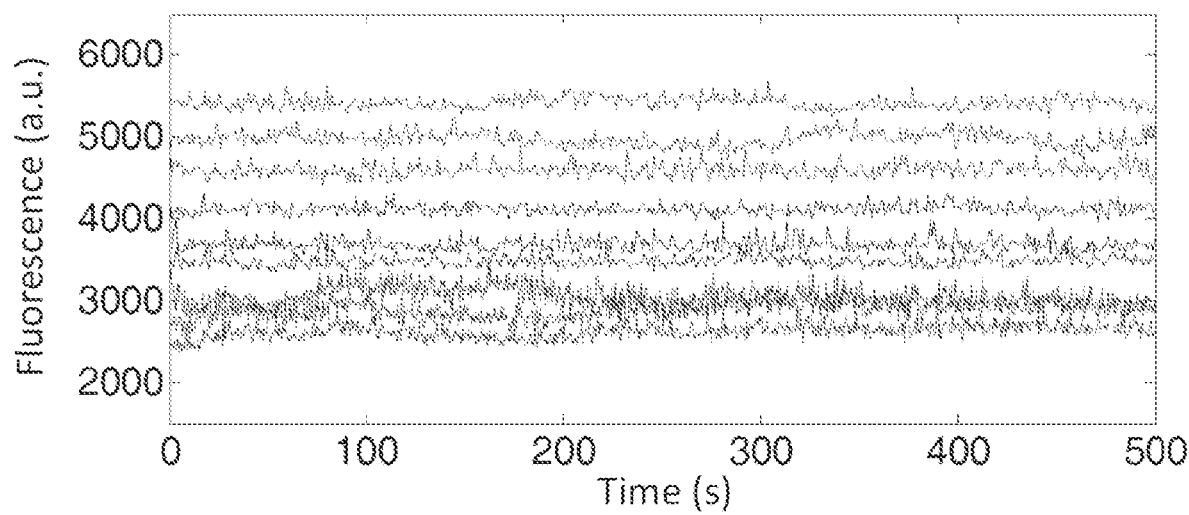

The NIR fluorescence response of the SWNT ratio sensors to $H_2O_2$ and NO in leaf sections was similar to experiments carried out in vitro (FIG. 3). Generally, the NIR quenching signal inside leaves for the 7,6 chiralities in both ratio sensors was not as steep as under in vitro conditions. This is most likely due to the passivation of SWNT surfaces with other biomolecules found in plant tissues during the infiltration through the leaf cross sections. As a negative control, the perfusion of water on the leaf surface caused no noticeable changes in the NIR fluorescence of 6,5 PVA-SWNT, 6,5 ss(AT)$_{15}$-SWNT and 7,6 ss(GT)$_{15}$-SWNT (FIGS. 8A and 8B). Together, these results indicate that the observed changes in SWNT photoluminescence are a result of the reaction of $H_2O_2$ and NO with the carbon nanotube surface.

Figure 6B:
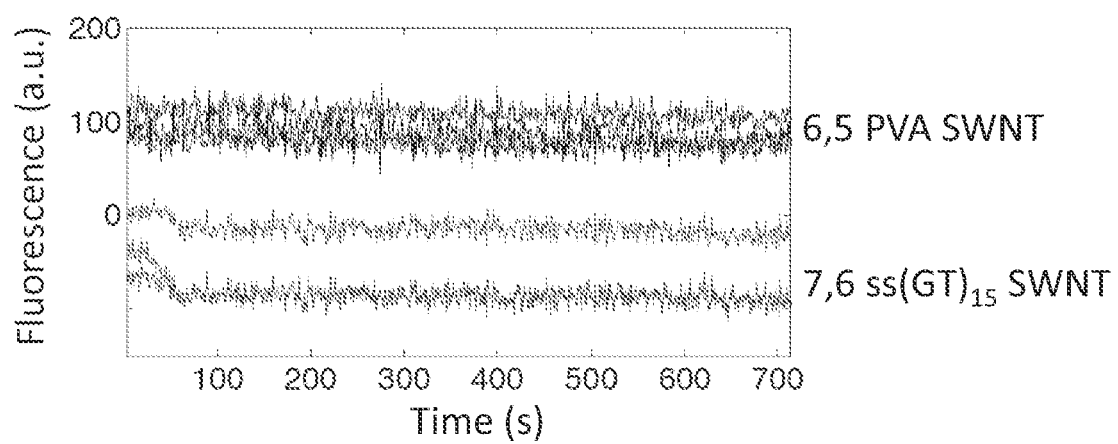
Figure 7A:
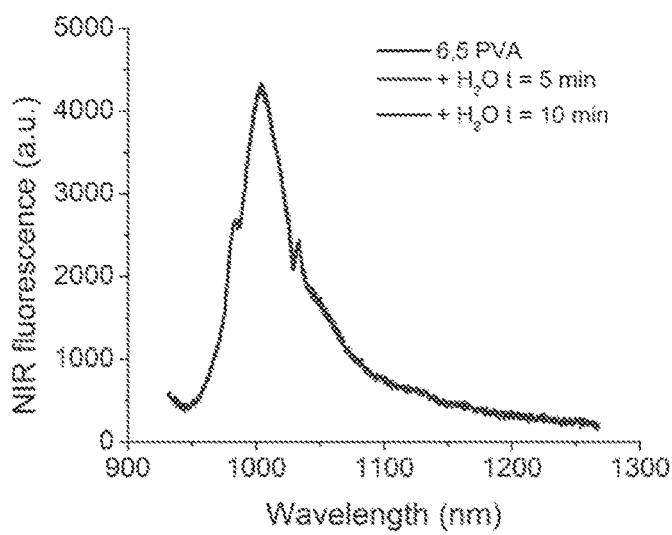
FIGS. 7A-7C are graphs showing single chirality SWNT response to water in vitro for 6,5 PVA (FIG. 7A), 6,5 $ss(AT)_{15}$ (FIG. 7B) and 7,6 $ss(GT)_{15}$ (FIG. 7C) slight changes in near infrared fluorescence upon addition to water.
Figure 7B:
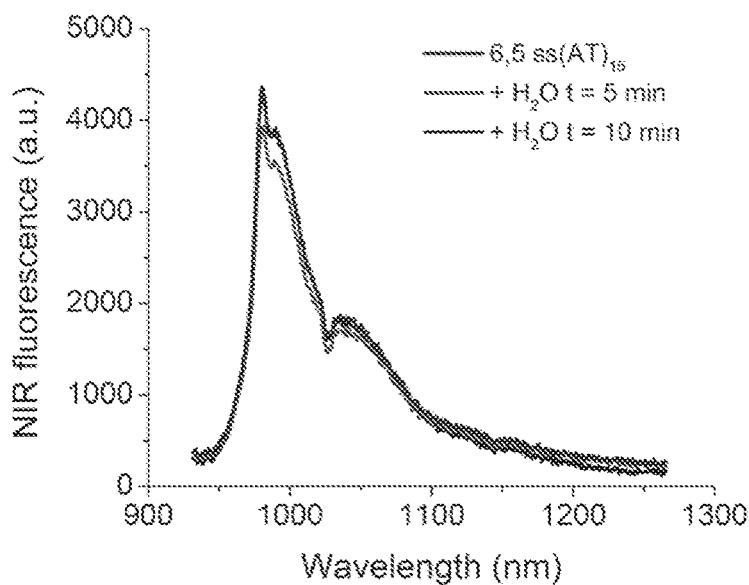
Figure 7C:
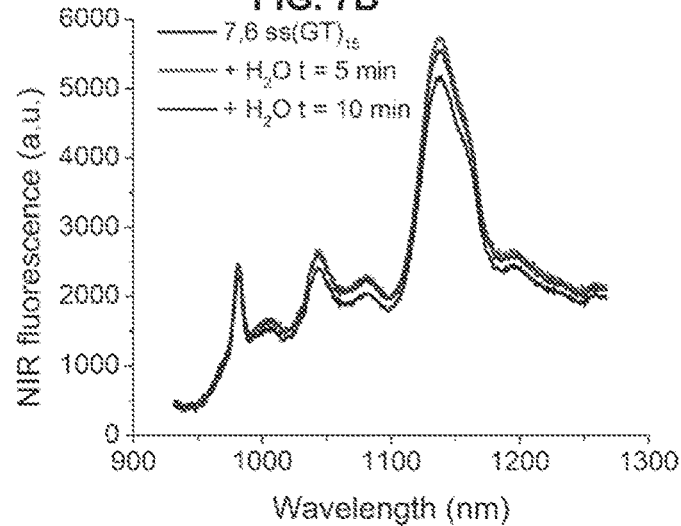

A temporal response of each SWNT chirality, 7,6 and 6,5, from within the tissues of infiltrated leaves was independently monitored. The in vivo ratiometric response was calculated as represented by equation (1) as the time-dependent change in the ratio of intensities between the initial 6,5 chirality intensity, which remains invariant, and the quenching 7,6 chirality, which is responsive to the analytes (FIGS. 5 and 6). For the in vivo imaging, a correction factor, $C_r$, was included to normalize the initial difference in the intensity between the two chiralities:

$$R_{7,6}(t) = C_r \frac{I_{6,5}(t)}{I_{7,6}(t)} \quad (1b)$$

Additionally, the internal reference variable $I_{6,5}^{norm}(t)$ was calculated as the time-dependent response of the reference chirality, the 6,5 SWNT, in the presence of the analytes by including in equation (2) the correction factor $C_r$:

$$I_{6,5}^{norm}(t) = C_r \frac{I_{6,5}(t)}{I_{6,5}(0)} \quad (2b)$$

In the presence of $H_2O_2$, a gradual increase of $R_{7,6}(t)$ for 7,6 ss(GT)$_{15}$ SWNT was observed (FIG. 5), as expected from the in vitro experiments. There is relatively little change in $I_{6,5}^{norm}$ in the leaf tissues after exposure to $H_2O_2$ as expected from the in vitro characterization of the $H_2O_2$ ratiometric sensor. Likewise, when the leaf sections were in the presence of NO, a gradual increase of $R_{7,6}(t)$ for 7,6 ss(GT)$_{15}$ SWNT (FIG. 6) was observed, as expected from the in vitro experiments. The internal reference for the NO ratio sensor, $I_{6,5}^{norm}$, remains invariant in the presence of NO throughout the course of the experiment.

The results of the ratiometric sensing experiments in leaf sections highlight the importance of having a dual-SWNT signal for in vivo sensing. It can be difficult to attribute selectivity to an analyte via an optical sensor response, particularly in the presence of other biomolecules that can also modify the dielectric environment of the SWNT. In particular, small reactive molecules such as reactive oxygen and nitrogen species are notoriously difficult to detect with high selectivity and sensitivity due to their short lifetimes fast diffusivities. The dual-chirality ratiometric sensor can provide a reference signal via non-responsive 6,5 SWNT to ensure that a quenching response in the 7,6 chirality SWNT is due to the intended analyte. Therefore, this ratiometric sensing platform is a powerful tool for the unambiguous detection of analytes in environments where interfering molecules are present in large quantities.

Plants interfaced with SWNT can be augmented to function as photonic chemical sensors. See, Giraldo, J. et al. Plant nanobionics approach to augment photosynthesis and biochemical sensing. Nat. Mater. 13, 400-408 (2014), which is incorporated by reference in its entirety. This nanobionic approach can enable plants that act as detectors of both NO and $H_2O_2$. Nanobionic plants with single chirality SWNT ratiometric sensors can provide a more robust platform to biochemical monitoring under changing field conditions. By multiplexing the NIR signal from plant chemical sentinels, remote detection of SWNT fluorescence in response to environmental factors can be separated from interactions with the analyte. Future stand-off detection of nanobionic plants will rely on SWNT chiralities able to report variations in NIR signal due to excitation intensity, angle of emission, and transmittance in the environment. A plant nanobionic monitoring with SWNT ratiometric platforms is a promising alternative to make self-repairing sentinels for biomolecules, hazardous chemicals, and pathogens in the environment.

The development of SWNT ratiometric sensors was facilitated by a rapid and efficient coating exchange method for single chirality SWNT separated in SDS. This technique enabled high throughput production of 6,5 and 7,6 SWNT sensors coated in polymers varying in their chemical structure and response to free radicals. The first double chirality SWNT ratiometric sensor was successfully built for hydrogen peroxide and nitric oxide, and this ratiometric SWNT platform in vivo is more selective to free radicals than their mixed chirality SWNT sensor counterparts. The response of the ratiometric sensor in living plant tissues was similar to tests under in vitro conditions, demonstrating the robustness of the carbon-based sensors for biological research applications. Expanding SWNT ratiometric platforms to multiple chiralities coated in diverse polymers can create nanosensors with exquisite selectivity and sensitivity. This nanobionic approach of interfacing living tissues with nanosensors may lead to self-repairing and self-powered plant biochemical detectors for signaling biomolecules, hazardous chemicals and pathogens in the environment.

Examples

Carbon Nanotube Suspension and Characterization

Figure 10A:
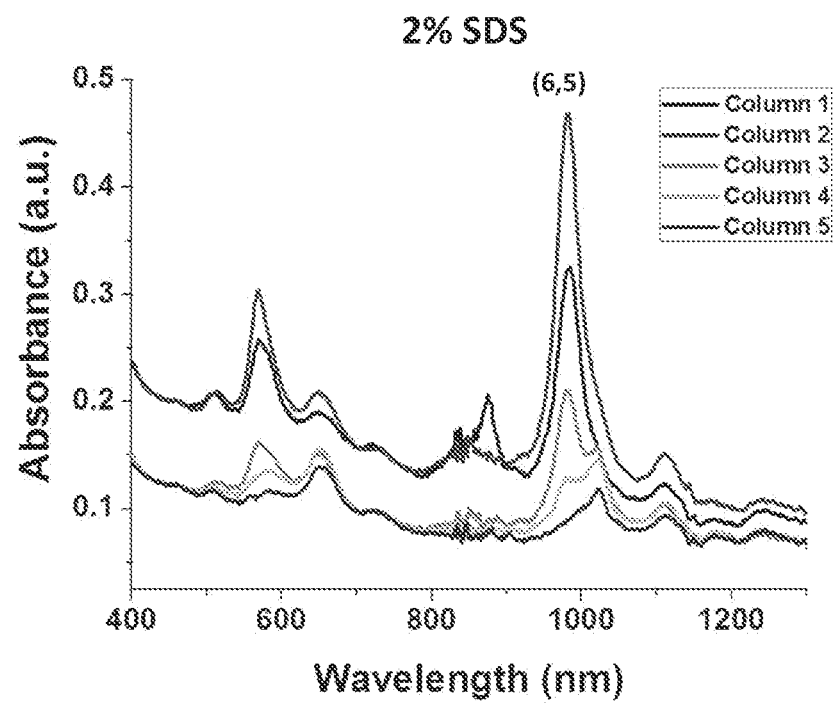
FIGS. 10A-10B are graphs showing automatic SWNT separation of 7,6 from 6,5 and 7,5 chiralities through sephacryl gel columns. First five columns of sephacryl gel remove 6,5 chirality SWNT in 2% SDS. The following columns, five to ten, separate 7,6 from 7,5 chirality using 1.5% SDS.
Figure 10B:
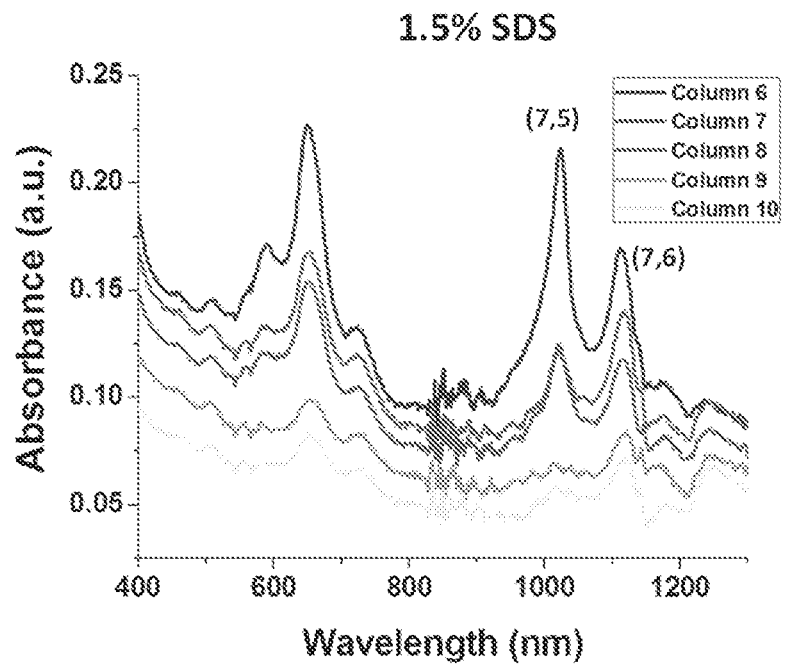

The 6,5 SDS SWNT were separated as previously reported. See, Tvrdy, K. et al. A kinetic model for the deterministic prediction of gel-based single-walled carbon nanotube separation. *ACS Nano* 7, 1779-1789 (2013), which is incorporated by reference in its entirety. The 7,6 SDS-SWNT suspension protocol was developed using a quantitative theory of adsorption separation of SWNT. See, Jain, R. M., Tvrdy, K., Han, R., Ulissi, Z. & Strano, M. S. Quantitative theory of adsorptive separation for the electronic sorting of single-walled carbon nanotubes. *ACS Nano* 8, 3367-79 (2014), which is incorporated by reference in its entirety. 100 mg of SWeNT 76 SWNTs (Southwest nanotechnologies) were suspended in 100 ml of 2% SDS by ½" tip sonication at 10 W for 13.5 hrs. The suspension was ultracentrifuged for 4 hr at 32000 RCF and 90% of the supernatant collected. Then 70 ml of the SWNT solution was filtered through 14 ml sephacryll columns previously equilibrated in SDS 2% (Columns 1-10), 1.5% (Columns 10-15) and 1% (Columns 15-20) at a flow rate of 3 ml/min (FIGS. 10A-10B). After passing the suspension through each column, The SWNT adsorbed to the sephacryll were eluted in 5% SDS by maintaining the flow at 5 ml/min.

Polycoated Single Chirality SWNT Synthesis and Characterization 2.5 mL of single-chirality SDS-SWNT were bath sonicated for 60 minutes, followed by 1 hour of centrifugation at 16,000 g to remove remaining SWNT bundles. The SDS-SWNT supernatant from the centrifugation product was transferred to a 5 mL glass vial and 10× mass excess of polymer relative to SWNT was added. The SDS-SWNT mixture was mixed via Pasteur pipetting then bath sonicated for 30 minutes. Subsequently, 3.5 mL of methanol was added dropwise, during which the mixture was removed from the bath sonicator, capped, and mixed by inversion after the addition of every 0.5 mL of methanol to ensure mixture of lower-density methanol with the higher-density SWNT solution. This process allows SDS to reach its critical micelle concentration, and enables the accompanying polymer to suspend the SWNT. The stability of the suspension was verified by centrifugation at 16,000 g for 10 minutes. The preparation was washed in 5-10 cycles of 1 minute each using a 100K Amicon centrifuge filter (Millipore) at 500-1000 rpm, depending on the polymer. The final suspension was re-suspended by mixing with a Pasteur pipette to its original volume of 2.5 mL in deionized water.

SWNT Ratiometric Sensor Response to Nitric Oxide and Hydrogen Peroxide In Vitro

The NIR fluorescence of the SWNT ratio sensor was monitored from 950 to 1250 nm under a laser excitation of 785 nm (Invictus) with a modified Axiovision Zeiss microscope (×20 objective) attached to an OMV InGaAs linear array spectrometer (Princeton Instruments). Single chirality SWNT 6,5 and 7,6 were mixed in a 300 ul well (BD falcon 96 well plate) to reach approximately similar peaks of intensity at 975-1025 nm and 1125-1150 nm, respectively. Changes in NIR fluorescence intensity were recorded every 20 s for 10 min after adding hydrogen peroxide and nitric oxide at 1:100 volume ratio. Final concentration of $H_2O_2$ and NO were 100 μM and 500 μM, respectively.

SWNT Leaf Infiltration

*Arabidopsis thaliana* leaf sections were taken by excising ~2 mm×2 mm sections of leaf tissue with a razor blade. Six leaf sections were mounted along an Ibidi μ-Slide (Ibidi, VI 0.4). A glass coverslip (No. 1, Fisher Scientific) was placed on top to create 6 individual flow channels with one leaf section per channel. 50 μl of PBS buffer was added to each channel. A ratiometric SWNT sensor was made by mixing equal concentrations of each the 6,5 and 7,6 chirality of polymer-SWNT together. 50 μl of the ratiometric sensor was added to each channel and allowed to incubate with leaf sections for 3 hours to enable SWNT diffusion into the leaf tissue. Then, 50 μl of PBS buffer was perfused through each channel to remove SWNT not permeated into leaf tissue.

Imaging SWNT Ratio Sensor In Vivo Inside Leaves in Real-Time

Ratiometric sensing videos were recorded in an Axio Vision inverted microscope (Zeiss) and imaged with an InGaAs OMA V 2D array detector (Princeton Instruments). The autofluorescence of chloroplast pigments in leaf sections was avoided by using a 785 nm Invictus photodiode laser (Kaiser) excitation source that is off-resonance with these pigments. Imaging of 6,5 chirality SWNTs was accomplished by using a 935/170 nm BrightLine single-band bandpass filter (Semrock, FF01-935/170-25) to capture only the emission of the 6,5 chirality SWNT. Imaging of the 7,6 SWNT was performed by using a 1100 nm long pass emission filter (Chroma) to capture only the emission of this SWNT chirality. There was no emission overlap between these two filter sets. Leaf sections were infiltrated as explained above with 6,5 and 7,6 ratio sensors, mounted within an Ibidi VI 0.4 slide, and fluorescence recorded at 0.5 s exposure per frame. Each chirality was imaged within a leaf section independent of the other chirality, and monitored the change in the SWNT intensity as a function of time upon addition of analyte. For the 7,6 chirality, its time-dependent response (R) was monitored against an invariant intensity from the reference 6,5 chirality at the initial experimental timepoint. For the 6,5 chirality, its time-dependent response (R) was monitored against the initial intensity from the 6,5 chirality, to ensure that the 6,5 chirality was indeed invariant upon addition of the analyte.

Nitric Oxide Solution

A saturated NO solution was prepared as previously described by Zhang et al. Briefly, 5 mL of $H_2O$ was added to two separate 10 mL round-bottom flasks (a control and an NO sample), which were then sealed with a septum. Two needles, a gas inlet needle terminated in the liquid and an outlet needle terminated in the dead space above the liquid, were place in the flask. Argon gas (Airgas) was bubbled into the $H_2O$ for 1 hr at an outlet pressure of 2 psi to remove dissolved oxygen. The control sample was removed from the system and the needles were removed. NO gas (99.99%, Electronicfluorocarbons) was then bubbled into the NO sample for 45 min, again at an outlet pressure of 2 psi. The final NO concentration of the sample was determined using the horseradish peroxidase assay. See, Kojima, H. et al. Detection and imaging of nitric oxide with novel fluorescent indicators: diaminofluoresceins. *Anal. Chem.* 70, 2446-53 (1998), and Kikuchi, K., Nagano, T. & Hirobe, M. Novel detection method of nitric oxide using horseradish peroxidase. *Biol. Pharm. Bull.* 19, 649-651 (1996), each of which is incorporated by reference in its entirety.

Other embodiments are within the scope of the following claims.

What is claimed is:

1. A composition comprising:
    a first plurality of nanoparticles having a first chirality, wherein the first plurality of nanoparticles comprise a first coating that is non-responsive to a particular analyte, and wherein the first plurality of nanoparticles exhibit a first emission when irradiated with electromagnetic radiation in the presence of the particular analyte; and a second plurality of nanoparticles having a second chirality, wherein the second plurality of nanoparticles comprise a second coating that is responsive to the particular analyte, and wherein the second plurality of nanoparticles exhibit a second emission when irradiated with electromagnetic radiation in the presence of the particular analyte;

wherein the first plurality of nanoparticles are configured to report a reference signal that is non-responsive to the analyte represented by the first emission and the second plurality of nanoparticles are configured to report an analyte-responsive signal represented by the second emission, and wherein the composition is configured to create a unique spectral signature for the particular analyte from a ratio of the first emission emitted from the first plurality of nanoparticles to the second emission emitted from the second plurality of nanoparticles.

2. The composition of claim 1, wherein the plurality of nanoparticles having both a first and second chirality include a nanotube.

3. The composition of claim 1, wherein the plurality of nanoparticles having both a first and second chirality include a carbon nanotube.

4. The composition of claim 1, wherein the plurality of nanoparticles having both a first and second chirality include a single-walled carbon nanotube.

5. The composition of claim 1, wherein the plurality of nanoparticles having both a first and second chirality include a polymer.

6. The composition of claim 5, wherein the polymer includes a polynucleotide.

7. The composition of claim 6, wherein the polynucleotide includes poly(AT).

8. The composition of claim 5, wherein the polymer includes a polysaccharide.

9. The composition of claim 8, wherein the polysaccharide is selected from the group consisting of dextran, pectin, hyaluronic acid, chitosan, and hydroxyethylcellulose.

10. The composition of claim 5, wherein the polymer includes poly(vinyl acid).

11. The composition of claim 1, wherein the plurality of nanoparticles having both a first and second chirality are photoluminescent.

12. The composition of claim 1, wherein the plurality of nanoparticles having both a first and second chirality emit near-infrared radiation.

13. The composition of claim 1, wherein each of the plurality of nanoparticles are photoluminescent and a photoluminescence emission of the photoluminescent nanoparticles is altered by a change in a stimulus.

14. The composition of claim 13, wherein the stimulus is a concentration of an analyte.

15. The composition of claim 14, wherein the analyte is a reactive oxygen species.

16. The composition of claim 14, wherein the analyte is nitric oxide.

17. The composition of claim 14, wherein the analyte is carbon dioxide.

18. The composition of claim 14, wherein the analyte is adenosine triphosphate.

19. The composition of claim 14, wherein the analyte is nicotinamide adenine dinucleotide phosphate.

20. The composition of claim 14, wherein the analyte is oxygen.

21. The composition of claim 13, wherein the stimulus is a pH of an organelle.

22. The composition of claim 1, wherein the first or second plurality of nanoparticles are carbon nanotubes.

23. A green plant including the composition of claim 1.

24. A method for monitoring activity in a sample, comprising: contacting a composition with a sample containing a particular analyte, wherein the composition comprises a first plurality of nanoparticles having a first chirality, wherein the first plurality of nanoparticles comprise a first coating that is non-responsive to a particular analyte, and wherein the first plurality of nanoparticles exhibit a first emission when irradiated with electromagnetic radiation in the presence of the particular analyte; and a second plurality of nanoparticles having a second chirality, wherein the second plurality of nanoparticles comprise a second coating that is responsive to the particular analyte, and wherein the second plurality of nanoparticles exhibit a second emission when irradiated with electromagnetic radiation in the presence of the particular analyte;

wherein the first plurality of nanoparticles are configured to report a reference signal that is non-responsive to the analyte represented by the first emission and the second plurality of nanoparticles are configured to report an analyte-responsive signal represented by the second emission;

measuring a photoluminescence emission of the composition at a first time point;

measuring the photoluminescence emission of the composition at a second time point wherein the second time point is after the first time point;

comparing the photoluminescence emission measured at the first time point to the photoluminescence emission measured at the second time point, wherein a change in the photoluminescence emission between the first time point and the second time point indicates a change in the particular analyte within the sample; and creating a unique spectral signature for the particular analyte by obtaining a ratio of the first emission emitted from the first plurality of nanoparticles to the second emission emitted from the second plurality of nanoparticles.

25. The method of claim 24, wherein the change in the photoluminescence emission includes a change in photoluminescence intensity, a change in peak wavelength, a Raman shift, or a combination thereof.

26. The method of claim 24, wherein the change in the particular analyte is a concentration change of the particular analyte.

27. The method of claim 26, wherein the particular analyte is a reactive oxygen species, nitric oxide, carbon dioxide, adenosine triphosphate, nicotinamide adenine dinucleotide phosphate, oxygen, or nitroaromatic compounds.

28. The method of claim 24, wherein the particular analyte is pH of an organelle.

29. A method for monitoring a sample, comprising:

introducing a plurality of first photoluminescent nanoparticles into the sample, wherein the first plurality of photoluminescent nanoparticles comprise a first coating that is non-responsive to a particular analyte, and wherein the first plurality of nanoparticles exhibit a first emission when irradiated with electromagnetic radiation in the presence of the particular analyte;

introducing a plurality of second photoluminescent nanoparticles into the sample, wherein the second plurality of photoluminescent nanoparticles comprise a second coating that is responsive to the particular analyte, and wherein the second plurality of nanoparticles exhibit a second emission when irradiated with electromagnetic radiation in the presence of the particular analyte; wherein the first plurality of nanoparticles are configured to report a reference signal that is non-responsive to the analyte represented by the first emission and the second plurality of nanoparticles are configured to report an analyte-responsive signal represented by the second emission;

measuring a photoluminescence emission of the first plurality of photoluminescent nanoparticles and the second plurality of photoluminescent nanoparticles at a first time point;

measuring the photoluminescence emission of the first plurality of photoluminescent nanoparticles and the second plurality of photoluminescent nanoparticles at a second time point wherein the second time point is after the first time point;

comparing the photoluminescence emission measured at the first time point to the photoluminescence emission measured at the second time point for the first plurality of photoluminescent nanoparticles;

comparing the photoluminescence emission measured at the first time point to the photoluminescence emission measured at the second time point for the second plurality of photoluminescent nanoparticles, wherein a change in the photoluminescence emission between the first time point and the second time point indicates a change in the particular analyte within the sample; and creating a unique spectral signature for the particular analyte by obtaining a ratio of the first emission emitted from the first plurality of nanoparticles to the second emission emitted from the second plurality of nanoparticles.

30. The method of claim 29, wherein a change in the photoluminescence emission includes a change in photoluminescence intensity, a change in peak wavelength, a Raman shift, or a combination thereof.

31. The method of claim 30, wherein the change in the particular analyte is a concentration change of the particular analyte.

32. The method of claim 31, wherein the particular analyte is a reactive oxygen species, nitric oxide, carbon dioxide, adenosine triphosphate, nicotinamide adenine dinucleotide phosphate, oxygen, or nitroaromatic compounds.

33. The method of claim 30, wherein the particular analyte is a pH of an organelle.

* * * * *